(12) United States Patent
White et al.

(10) Patent No.: US 10,973,672 B2
(45) Date of Patent: Apr. 13, 2021

(54) COMPRESSION BELTS FOR SELECTIVE CHEST COMPRESSION FOLLOWING THORACIC AND CARDIOTHORACIC SURGERY AND FOR RIB FRACTURE STABILIZATION

(71) Applicant: PELVICBINDER, INC., Dallas, TX (US)

(72) Inventors: Leslie D. White, Dallas, TX (US); Michael W. Freitas, Colleyville, TX (US)

(73) Assignee: PELVICBINDER, INC., Dallas, TX (US)

( * ) Notice: Subject to any disclaimer, the term of this patent is extended or adjusted under 35 U.S.C. 154(b) by 378 days.

(21) Appl. No.: 16/152,138

(22) Filed: Oct. 4, 2018

(65) Prior Publication Data

US 2019/0029865 A1 Jan. 31, 2019

Related U.S. Application Data

(63) Continuation-in-part of application No. 14/987,544, filed on Jan. 4, 2016, now Pat. No. 10,092,440.

(60) Provisional application No. 62/152,586, filed on Apr. 24, 2015.

(51) Int. Cl.
*A61F 5/02* (2006.01)
*A61F 5/03* (2006.01)
*A61F 5/30* (2006.01)

(52) U.S. Cl.
CPC ............... *A61F 5/02* (2013.01); *A61F 5/03* (2013.01); *A61F 5/30* (2013.01)

(58) Field of Classification Search
CPC .. A61F 5/02; A61F 5/022; A61F 5/024; A61F 5/026; A61F 5/028; A61F 5/37; A61F 5/05808; A61F 5/03; A61F 5/30; A61F 2007/0024; A61F 2007/0025; A61F 2007/0026; A61F 2007/0027
See application file for complete search history.

(56) References Cited

U.S. PATENT DOCUMENTS

| | | |
|---|---|---|
| 5,226,874 A | 7/1993 | Heinz et al. |
| 5,346,461 A | 9/1994 | Heinz et al. |
| RE35,940 E | 10/1998 | Heinz et al. |
| 6,602,214 B2 | 5/2003 | Heinz et al. |

(Continued)

*Primary Examiner* — Tarla R Patel

(57) ABSTRACT

A compression belt encircles a selected portion of a patient's body to provide temporary compression. The compression belt comprises an elongated belt body having first and second free ends free, a tensioning cord, a handle attached to the end of the tensioning cord, closing mechanism providing a mechanical advantage, a one-way tension mechanism and a selective release mechanism. Pulling the handle causes the closing mechanism to pull the first and second free ends closer together to compress the patient's body and engage the one-way tension mechanism that maintains compression even in the absence of continued pulling of the handle, unless the selective release mechanism is activated to release the compression. A buffer made of compressible material can be attached to the underside of the belt body to provide inward pressure when the belt is tightened. The belt body can further include a respiratory expansion panel that elongates elastically under tension.

20 Claims, 20 Drawing Sheets

(56) References Cited

U.S. PATENT DOCUMENTS

| | | | |
|---|---|---|---|
| 7,727,172 B2 * | 6/2010 | Wang | A61F 5/028 602/19 |
| 8,372,023 B2 * | 2/2013 | Garth | A61F 5/028 128/876 |
| 10,092,440 B2 | 10/2018 | White et al. | |

* cited by examiner

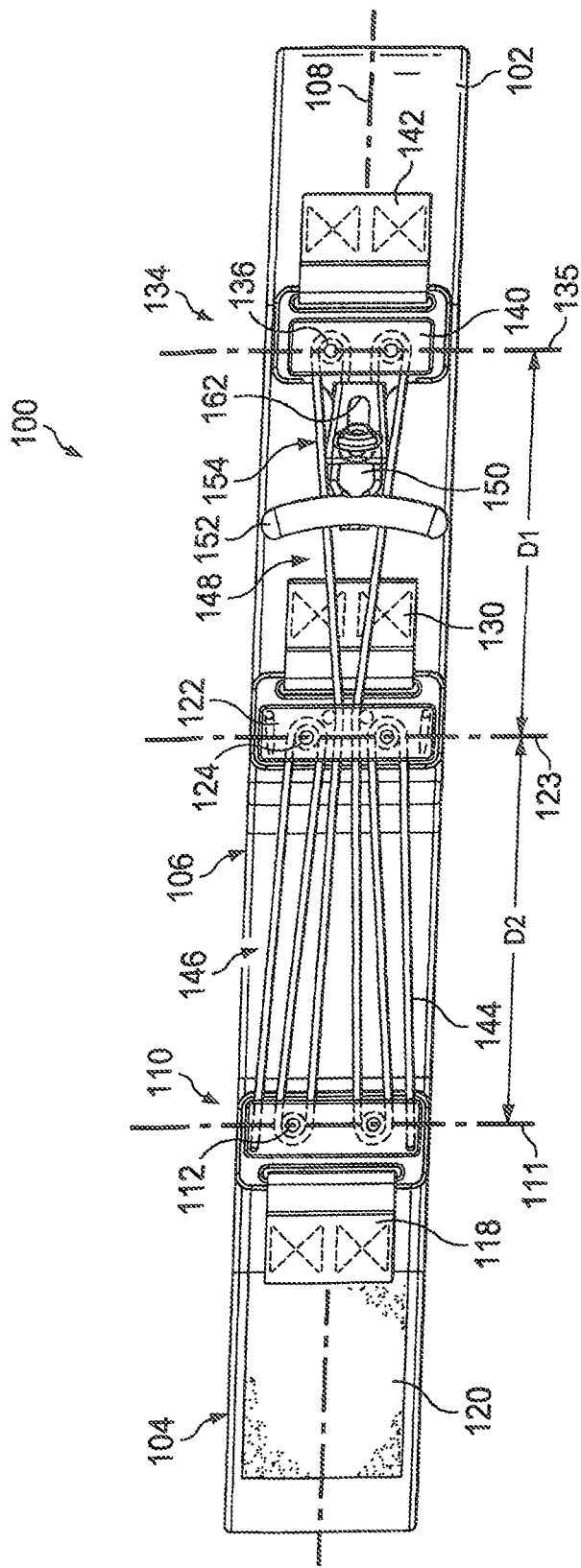

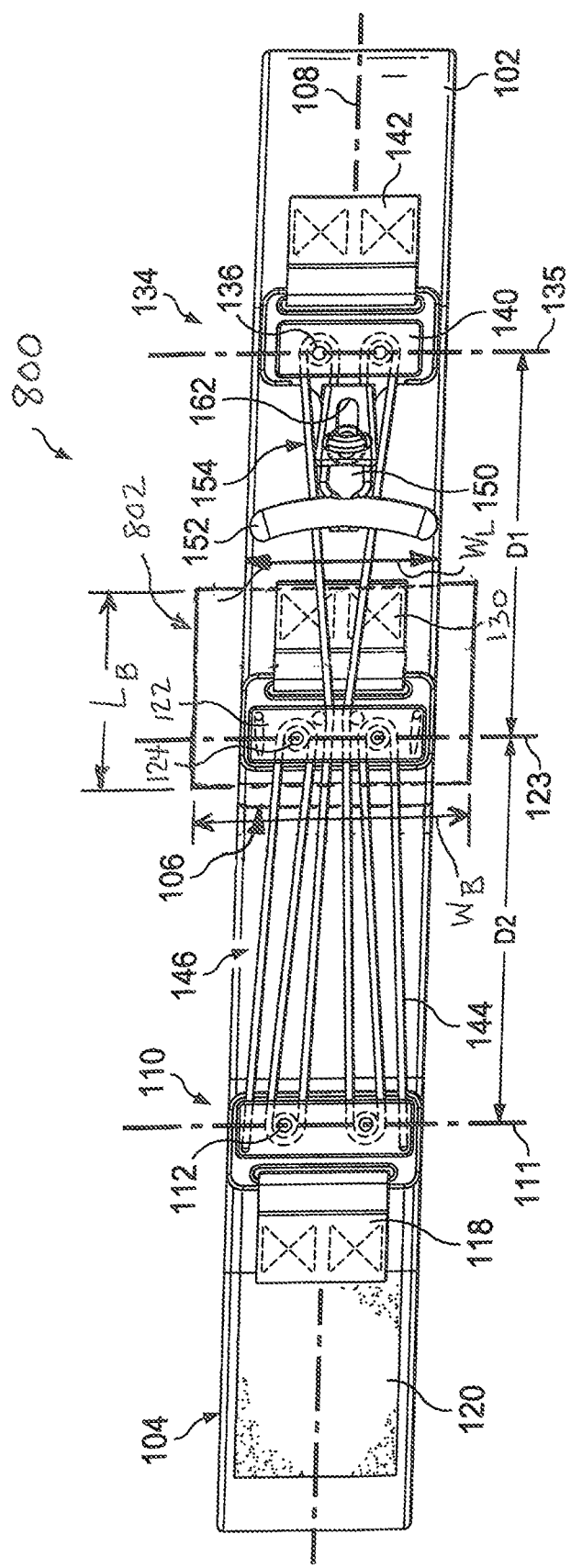

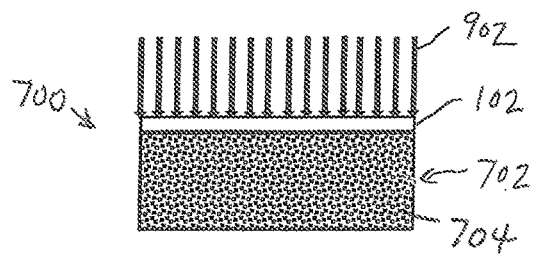
FIG. 9A
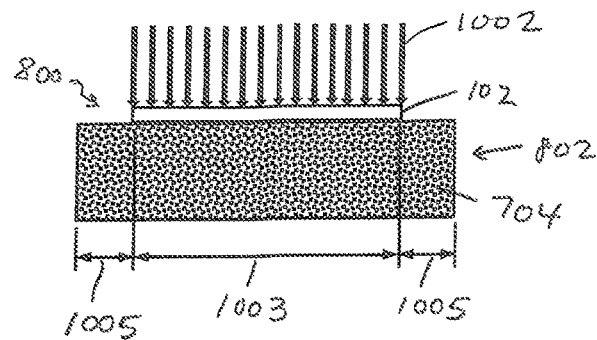
FIG. 10A
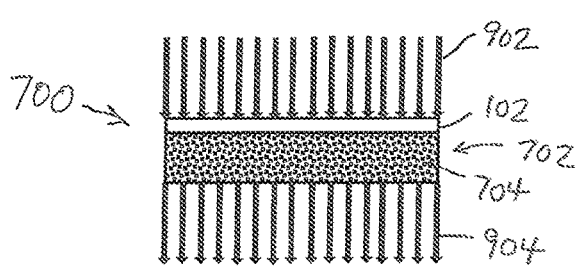
FIG. 9B
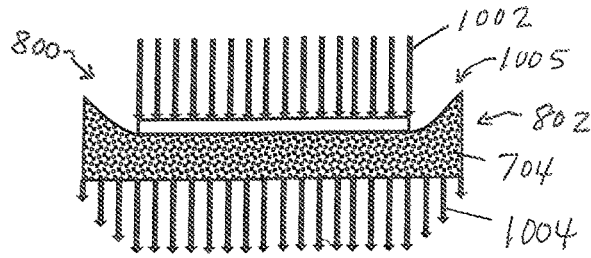
FIG. 10B
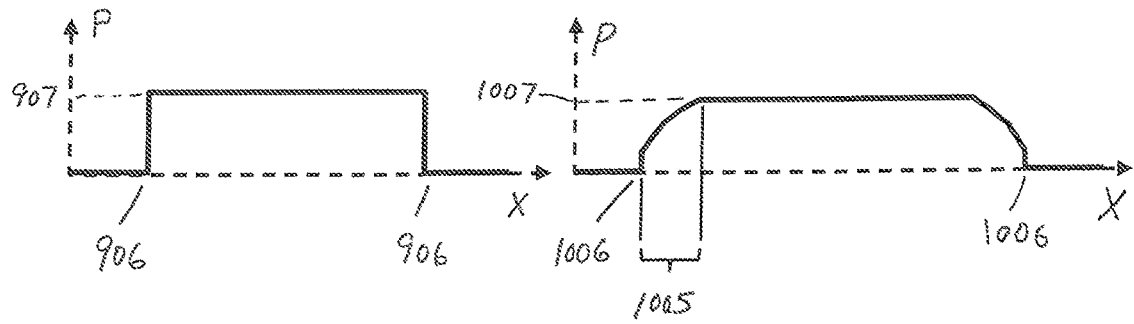
FIG. 9C
FIG. 10C

COMPRESSION BELTS FOR SELECTIVE CHEST COMPRESSION FOLLOWING THORACIC AND CARDIOTHORACIC SURGERY AND FOR RIB FRACTURE STABILIZATION

CROSS-REFERENCE TO RELATED APPLICATIONS

This application is a Continuation-In-Part of U.S. patent application Ser. No. 14/987,544, filed Jan. 4, 2016, published as U.S. Patent Application Publication No. 2016/0310310, which claims benefit of U.S. Provisional Application No. 62/152,586, filed Apr. 24, 2015, the specifications of which are hereby incorporated by reference in their entirety.

TECHNICAL FIELD

The following disclosure relates to medical compression belts which may be used in post-surgical treatment of patients following, e.g., thoracic, cardiothoracic and abdominal surgeries, for stabilization of rib fractures, or for emergency stabilization of pelvic fractures. More particularly, it relates to medical compression belts fitted around a selected portion of a patient's torso, which belts can be selectively activated by the patient or technician for the temporary compression of the selected body portion and selective released by the patent or technician to end the compression.

BACKGROUND

The cardiac pillow, also known as the "heart pillow" or "cough pillow," is a therapeutic tool utilized by doctors, nurses and patients after heart surgery or other types of thoracic surgery. The cardiac pillow is a small conventional pillow often, but not always, configured in the shape of a "valentine" style heart and given to patients shortly after their heart surgery or thoracic surgery. Typically, the patent is told to temporarily press or clutch the cardiac pillow against the chest area (i.e., using the patient's own arms and hands) when sitting up, coughing, standing up or engaging in other activities that may cause discomfort to the surgery area. Used in this manner, the cardiac pillow splints the fracture in the sternum when the patient moves or breathes to lessen the patient's pain or discomfort.

There are drawbacks to the use of cardiac pillows for some patients. The cardiac pillow may become misplaced on the bed or even fall off the bed, preventing the patient from reaching it in time when needed. Some patients may not have sufficient arm or hand strength to press the pillow against the chest effectively. Further, when patients become mobile, e.g., using a walker, they do not have free hands to carry and/or use the cardiac pillow, because they must use both hands to grip the walker for safety. A need therefore exists, for a therapeutic device that can provide temporary chest compression to post-surgical thoracic patients while addressing some of the drawbacks encountered with the cardiac pillow.

Patients recovering from abdominal surgery may face medical issues similar, though not identical, to post-thoracic/cardiothoracic patents. Besides pain or discomfort caused by when sitting up, coughing, standing up, etc., abdominal patients may face the further risk of rupturing their sutures or incisions. This is especially true for obese patients. In such cases, temporary cardiac pillow type therapies may not be effective for reasons outlined above. In some cases, a conventional belt may be used to provide extra support to the abdomen; however, such belts may be uncomfortable for extended wear. A need therefore exists, for a therapeutic device that can provide temporary abdominal compression to post-surgical abdominal patients while addressing some of the drawbacks encountered with the cardiac pillow and conventional belts.

Other chest compression devices are known for the stabilization of rib fractures and pelvic compression devices are known for the emergency stabilization of pelvic fractures. Such devices often have a belt configuration with a length adjustment mechanism. However, operation of the length adjustment mechanisms of conventional devices may be complicated and/or inconvenient, making it difficult for a technician to fit the belt to the patient, and difficult to apply or release compression after the belt is fitted. A need therefore exists, for chest compression devices and pelvic compression devices that are easier to fit and operate.

SUMMARY

In one aspect thereof, a compression belt is provided for encircling a selected portion of a patient's body and providing temporary circumferential compression of the selected portion of the patient's body. The compression belt comprises an elongated belt body having a continuous length with opposing first and second free end portions and defining a centerline extending therebetween. The belt body is adapted to be wrapped circumferentially around the selected portion of the patient's body. A first pulley bank is affixed to the first end portion, the first pulley bank including at least two pulleys arranged perpendicular to the centerline of the belt body. A second pulley bank is affixed to the second end portion, the second pulley bank including at least two pulleys arranged perpendicular to the centerline of the belt body. A third pulley bank is affixed to the belt body at a fixed distance from the second pulley bank, the third pulley bank including at least two pulleys arranged perpendicular to the centerline of the belt body. A flexible cord interconnects the first, second and third pulley banks, the cord having a first cord portion extending between the pulleys of the first and second pulley banks in alternation, a second cord portion connected to the first cord portion and extending between the pulleys of the first and third pulley banks, and a third cord portion connected to the second cord portion and extending away from the third pulley bank. A handle is connected to the third cord portion, whereby withdrawing the third cord portion from the third pulley bank by pulling the handle away from the third pulley bank causes a shortening of the first cord portion such that the first and second pulley banks move closer together along with the first and second free end portions to which the respective pulley banks are affixed, thereby tightening the belt body around the selected portion of the patient's body and compressing the selected portion of the patient's body. A selectively releasable one-way cord lock mechanism is connected to the belt body, the cord lock mechanism including a frame defining a cord passage through which the third cord portion is routed after leaving the third pulley bank, a locking member mounted in the frame and movable between a locked position and a released position, the third cord portion being routed against the locking member so as to bias the locking member toward the locked position, and a release member connected to the locking member for moving the locking member between the locked position and the released position. The locking member, when in either the locked position or the released position, allows withdrawal of the third cord portion from the third pulley bank to compress the selected portion of the patient's body, when in the locked position, prevents the third cord portion from retracting into the third pulley bank to maintain compression of the selected portion of the patient's body, and when in the released position, allows the third cord portion to retract into the third pulley bank to discontinue compression of the selected portion of the patient's body.

In another aspect thereof, a compression belt encircles a selected portion of a patient's body and provides temporary compression of the selected portion. The compression belt comprises an elongated belt having first and second free ends free, a tensioning cord, a handle attached to the end of the tensioning cord, closing mechanism providing a mechanical advantage, a one-way tension mechanism and a selective release mechanism. Pulling the handle causes the closing mechanism to pull the first and second free ends closer together so as to compress the selected portion of the patient's body, the one-way tension mechanism maintains compression of the patient's body, even in the absence of continued pulling of the handle, unless the selective release mechanism is activated, and activating the selected release mechanism releases the compression of the patient's body.

In still another aspect, a compression belt is provided for encircling a selected portion of a patient's body and providing temporary circumferential compression of the selected portion of the patient's body. The compression belt comprises an elongated belt body having a continuous length with opposing first and second free end portions and defining a centerline extending therebetween. The belt body is adapted to be wrapped circumferentially around the selected portion of the patient's body. A first pulley bank is affixed to the first end portion, the first pulley bank including at least two pulleys arranged perpendicular to the centerline of the belt body. A second pulley bank is affixed to the second end portion, the second pulley bank including at least two pulleys arranged perpendicular to the centerline of the belt body. A third pulley bank is affixed to the belt body at a fixed distance from the second pulley bank, the third pulley bank including at least two pulleys arranged perpendicular to the centerline of the belt body. A flexible cord interconnects the first, second and third pulley banks, the cord having a first cord portion extending between the pulleys of the first and second pulley banks in alternation, a second cord portion connected to the first cord portion and extending between the pulleys of the first and third pulley banks, and a third cord portion connected to the second cord portion and extending away from the third pulley bank. A handle is connected to the third cord portion, whereby withdrawing the third cord portion from the third pulley bank by pulling the handle away from the third pulley bank causes a shortening of the first cord portion such that the first and second pulley banks move closer together along with the first and second free end portions to which the respective pulley banks are affixed, thereby circumferentially tightening the belt body around the selected portion of the patient's body and circumferentially compressing the selected portion of the patient's body. A buffer is attached to an inner surface of the body belt, the buffer being formed of a flexible and compressible material having a width $W_B$ measured in a direction parallel to the lateral width $W_L$ of the belt body, a length $L_B$ measured in a direction parallel to the centerline of the belt body, and a thickness $T_B$ measured perpendicular to $W_B$ and $T_B$. Circumferential tightening of the belt body causes compression of the compressible material of the buffer in the thickness direction against an adjacent portion of the patient's body, wherein an inward pressure is exerted on the adjacent portion of the patient's body by the buffer.

In one embodiment, the buffer is formed of a plastic foam material having a density in the range from 1.1 pounds per cubic foot to 1.5 pounds per cubic foot and an indentation load deflection (ILD) in the range from 50 pounds to 80 pounds.

In another embodiment, the buffer has a width $W_B$ less than or equal to the lateral width $W_L$ of the belt body.

In yet another embodiment, the buffer has a width $W_B$ greater than 1.25 times the lateral width $W_L$ of the belt body.

In still another embodiment, the buffer has a rectangular configuration with a uniform width $W_B$ and a uniform length $L_B$.

In a further embodiment, the buffer has a heart-shaped configuration that is at least partially visible from the front side of the belt body.

In a still further embodiment, the heart-shaped buffer has a width $W_B$ at least 1.4 times the lateral width $W_L$ of the belt body.

In another embodiment, the heart shaped buffer has a visible red color.

In yet another embodiment, the heart shaped buffer is formed of an unjacketed plastic foam material having a density of at least 1.3 pounds per cubic foot and an indentation load deflection (ILD) of at least 70 pounds.

In still another embodiment, the heart shaped buffer includes a fabric or plastic jacket over the flexible material.

In a further embodiment, the compression belt further comprises a selectively releasable one-way cord lock mechanism connected to the belt body, the cord lock mechanism including a frame defining a cord passage through which the third cord portion is routed after leaving the third pulley bank, a locking member mounted in the frame and movable between a locked position and a released position, the third cord portion being routed against the locking member so as to bias the locking member toward the locked position, and a release member connected to the locking member for moving the locking member between the locked position and the released position. The locking member, when in either the locked position or the released position, allows withdrawal of the third cord portion from the third pulley bank to compress the selected portion of the patient's body, when in the locked position, prevents the third cord portion from retracting into the third pulley bank to maintain compression of the selected portion of the patient's body, and when in the released position, allows the third cord portion to retract into the third pulley bank to discontinue compression of the selected portion of the patient's body.

In yet another aspect, a compression belt is provided for encircling a selected portion of a patient's body and providing temporary circumferential compression of the selected portion of the patient's body. The compression belt comprises an elongated belt body having a continuous length with opposing first and second free end portions and defining a centerline extending therebetween. The belt body is adapted to be wrapped circumferentially around the selected portion of the patient's body. A first pulley bank is affixed to the first end portion, the first pulley bank including at least two pulleys arranged perpendicular to the centerline of the belt body. A second pulley bank is affixed to the second end portion, the second pulley bank including at least two pulleys arranged perpendicular to the centerline of the belt body. A flexible cord interconnects the first and second pulley banks, the cord having a first cord portion extending between the pulleys of the first and second pulley banks in alternation and a second cord portion connected to the first cord portion and extending away from the second pulley bank. A handle is connected to the second cord portion, whereby withdrawing the second cord portion from the second pulley bank by pulling the handle causes a shortening of the first cord portion such that the first and second pulley banks move closer together along with the first and second free end portions to which the respective pulley banks are affixed, thereby circumferentially tightening the belt body around the selected portion of the patient's body and circumferentially compressing the selected portion of the patient's body. A buffer is attached to an inner surface of the body belt, the buffer being formed of a flexible and compressible material having a width $W_B$ measured in a direction parallel to the lateral width $W_L$ of the belt body, a length $L_B$ measured in a direction parallel to the centerline of the belt body, and a thickness $T_B$ measured perpendicular to $W_B$ and $T_B$. Circumferential tightening of the belt body causes compression of the compressible material of the buffer in the thickness direction against an adjacent portion of the patient's body, wherein an inward pressure is exerted on the adjacent portion of the patient's body by the buffer.

In one embodiment, the buffer has a width $W_B$ less than or equal to the lateral width $W_L$ of the belt body.

In another embodiment, the buffer has a width $W_B$ greater than 1.25 times the lateral width $W_L$ of the belt body.

In yet another embodiment, the buffer has a heart-shaped configuration that is at least partially visible from the front side of the belt body.

In a further aspect, a compression belt is provided for encircling a selected portion of a patient's body and providing temporary circumferential compression of the selected portion of the patient's body. The compression belt comprises an elongated belt body having a continuous length with opposing first and second free end portions and defining a centerline extending therebetween. The belt body is adapted to be wrapped circumferentially around the selected portion of the patient's body. A first pulley bank is affixed to the first end portion, the first pulley bank including at least two pulleys arranged perpendicular to the centerline of the belt body. A second pulley bank is affixed to the second end portion, the second pulley bank including at least two pulleys arranged perpendicular to the centerline of the belt body. A third pulley bank is affixed to the belt body at a fixed distance from the second pulley bank, the third pulley bank including at least two pulleys arranged perpendicular to the centerline of the belt body. A flexible cord interconnects the first, second and third pulley banks, the cord having a first cord portion extending between the pulleys of the first and second pulley banks in alternation, a second cord portion connected to the first cord portion and extending between the pulleys of the first and third pulley banks, and a third cord portion connected to the second cord portion and extending away from the third pulley bank. A handle is connected to the third cord portion, whereby withdrawing the third cord portion from the third pulley bank by pulling the handle away from the third pulley bank causes a shortening of the first cord portion such that the first and second pulley banks move closer together along with the first and second free end portions to which the respective pulley banks are affixed, thereby circumferentially tightening the belt body around the selected portion of the patient's body and circumferentially compressing the selected portion of the patient's body. The belt body further includes at least one respiratory expansion panel having an original length $L_O$ that can stretch elastically in the centerline direction to a maximum length $L_{Max}$ when circumferential tension is applied to the belt body and can return to the original length $L_O$ when the circumferential tension is released.

In one embodiment, the respiratory expansion panel is a section of elastic fabric that spans the full width of the belt body and is joined to the other portions of the belt body using overlapping seams and stitching.

In another embodiment, the respiratory expansion panel has an original length $L_O$ greater than 2 inches and a stretch rate SR of at least 80%.

In yet another embodiment, the at least one respiratory expansion panel has a total elongation $L_{Tot}$ greater than or equal to 3.4 inches.

BRIEF DESCRIPTION OF THE DRAWINGS

For a more complete understanding, reference is now made to the following description taken in conjunction with the accompanying Drawings in which:

FIGS. 3A and 3B are, respectively, a top view and a side view of the compression belt of FIG. 1;

FIGS. 7A-7C show a compression belt for selective temporary chest compression and localized pressure enhancement in accordance with another aspect, wherein FIG. 7A is a perspective view thereof, FIG. 7B is a top view thereof and FIG. 7C is a side view thereof;

FIGS. 8A-8B show a compression belt for selective temporary chest compression and localized pressure enhancement in accordance with yet another aspect, wherein FIG. 8A is a perspective view thereof and FIG. 8B is a top view thereof;

FIGS. 9A-9C show schematic force and pressure diagrams of a compression belt with a full-width buffer, wherein FIG. 9A shows the forces applied to the buffer by the belt, FIG. 9B shows the force transmitted to the user when the buffer is compressed by the belt against the user, and FIG. 9C shows the pressure distribution on the user's body;

FIGS. 10A-10C show schematic force and pressure diagrams of a compression belt with an over-width buffer, wherein FIG. 10A shows the forces applied to the buffer by the belt, FIG. 10B shows the force transmitted to the user when the over-width buffer is compressed by the belt against the user, and FIG. 10C shows the pressure distribution on the user's body;

FIGS. 11A-11C show a compression belt for selective temporary chest compression and localized pressure enhancement in accordance with still another aspect, wherein FIG. 11A is a perspective view thereof, FIG. 11B is a top view thereof and FIG. 11C is a side view thereof;

FIGS. 13A and 13B show a compression belt in accordance with another aspect, wherein FIG. 13A is a perspective view thereof and FIG. 13B is a side view thereof.

DETAILED DESCRIPTION

Figure 1:
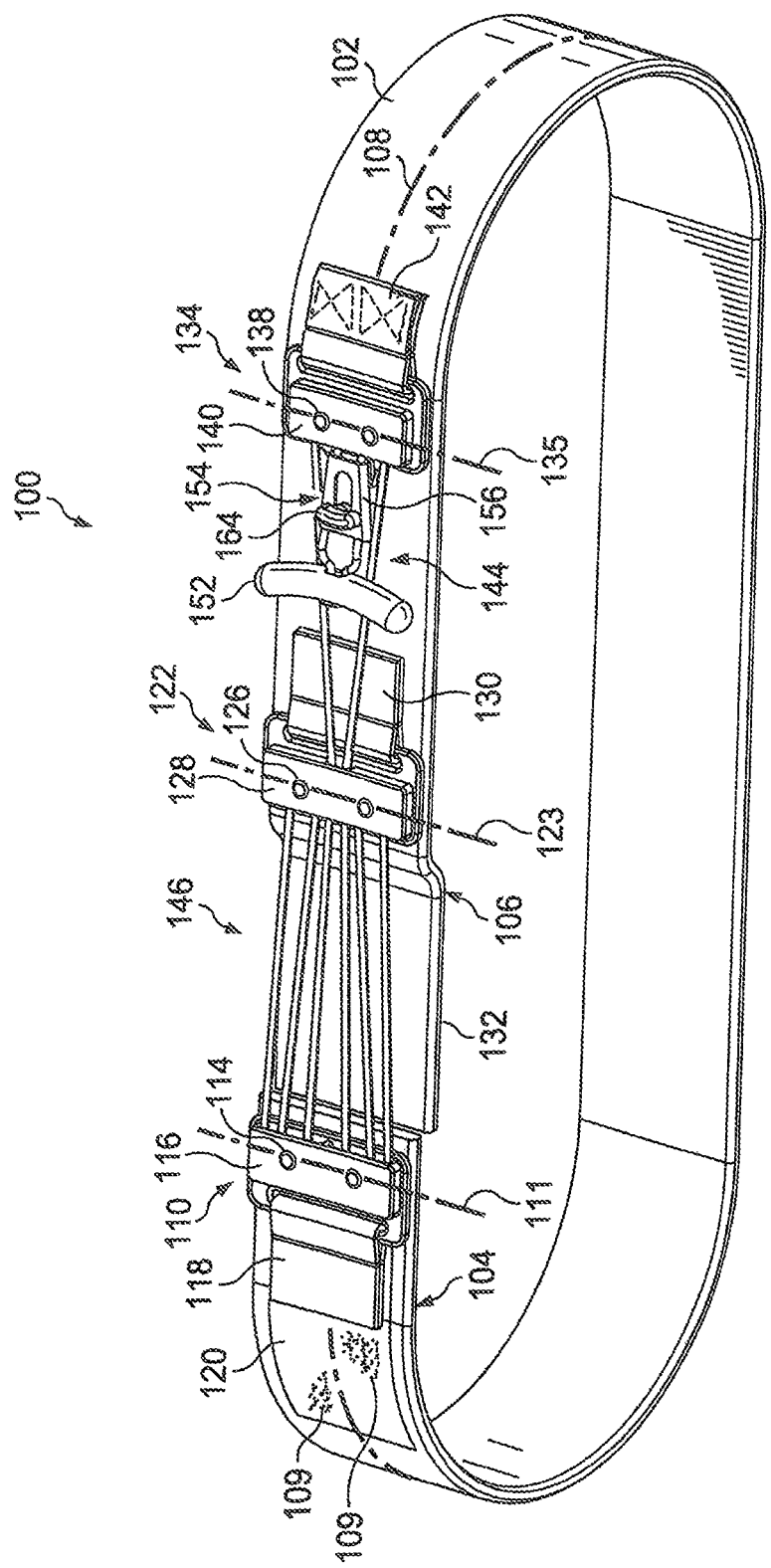
FIG. 1 shows a perspective view of a compression belt for selective temporary chest compression in accordance with one aspect.

Referring now to the drawings, wherein like reference numbers are used herein to designate like elements throughout, the various views and embodiments of compression belts for selective chest compression following thoracic and cardiothoracic surgery, for selective abdominal compression following abdominal surgery, for stabilization of rib fractures, or for emergency stabilization of pelvic fractures are illustrated and described, and other possible embodiments are described. The figures are not necessarily drawn to scale, and in some instances the drawings have been exaggerated and/or simplified in places for illustrative purposes only. One of ordinary skill in the art will appreciate the many possible applications and variations based on the following examples of possible embodiments.

Referring now to FIG. 1, there is illustrated a perspective view of a compression belt for selective temporary compression of a patient's chest, abdomen, pelvis or other body portion in accordance with one aspect. The compression belt 100 includes an elongated belt body 102 having a continuous length with opposing first and second free end portions 104, 106 and defining a centerline 108 extending therebetween. The belt body 102 is adapted to be wrapped circumferentially around a selected portion of the patient's body. The belt body 102 is preferably made from a fabric material that is lightweight, strong in tension, and flexible enough to be comfortable when worn for long periods of time. Selected areas of the belt body 102 may be provided with attachment material 109 to facilitate attaching or affixing other components of the belt 100 to the belt body. In particular, attachment material 109 (represented by partially patterned area) may comprise hook-and-loop type fastening material (e.g., VELCRO® brand fastening material) mounted on selected areas of the belt 100. The hook-and-loop material may comprise hook-type material, loop-type material and or both hook- and loop-type material.

In a preferred embodiment of the compression belt 100, the belt body 102 may have an overall width (measured perpendicular to the centerline 108) of about 3.0 inches and a length (measured along the centerline) of about 60 inches. If necessary, the belt body 102 may be trimmed for better fit to the patient by cutting one or both of the free end portions 104, 106. As further described below, certain elements of the compression belt 100 may be releasably affixed to the belt body 102 to facilitate trimming the belt to fit. In a preferred embodiment, the compression belt 100 will provide up to 8.0 inches of compression (this being the initial distance D2 between the first and second pulley banks described below).

Figure 2:
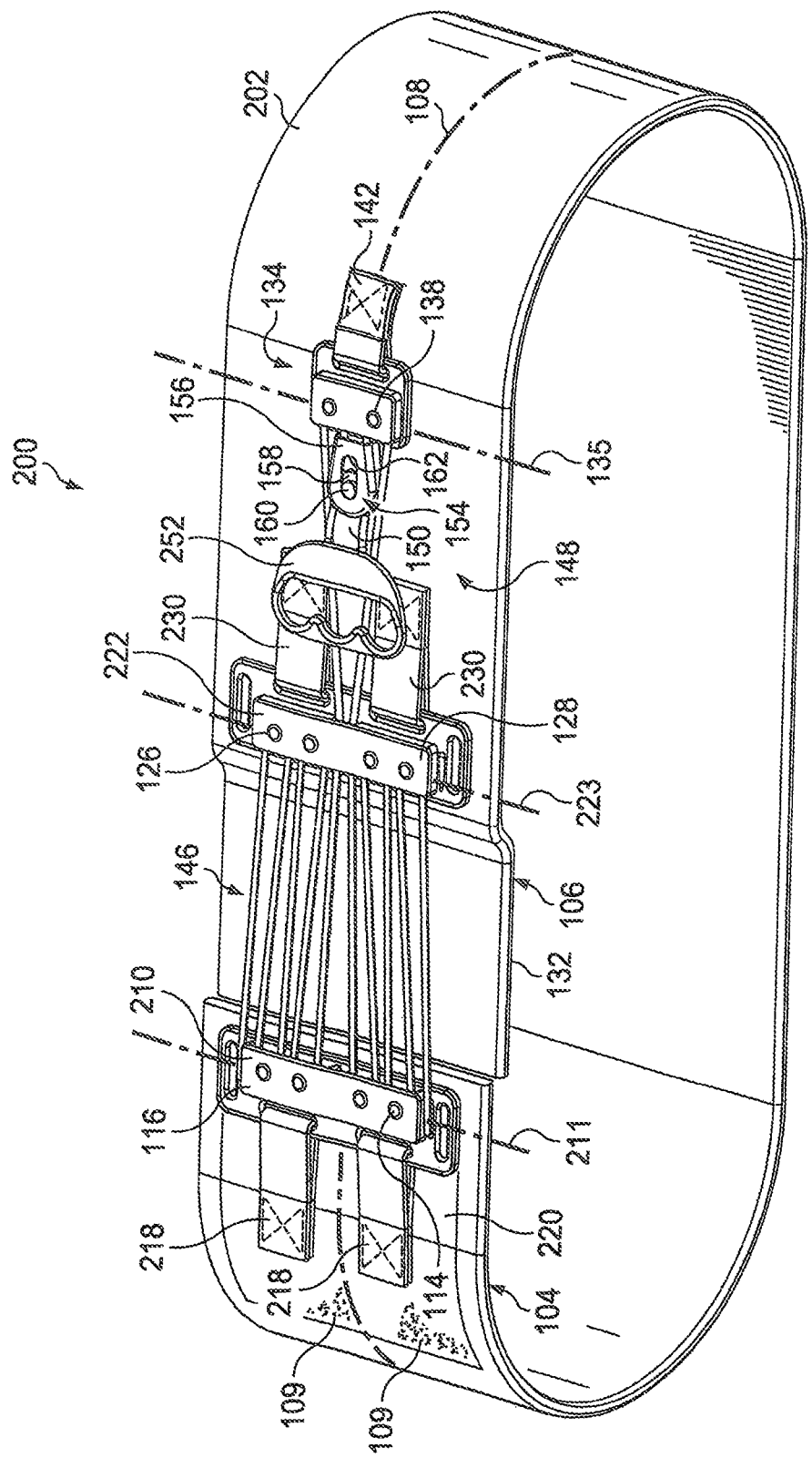
FIG. 2 shows a perspective view of a compression belt for selective temporary abdominal compression in accordance with another aspect.

Referring now to FIG. 2, there is illustrated a perspective view of a compression belt for selective temporary compression of a patient's abdomen, ribs, pelvis or other body portion in accordance with another aspect. The compression belt 200 will be described in greater detail below following the description of the first aspect.

Figure 3B:
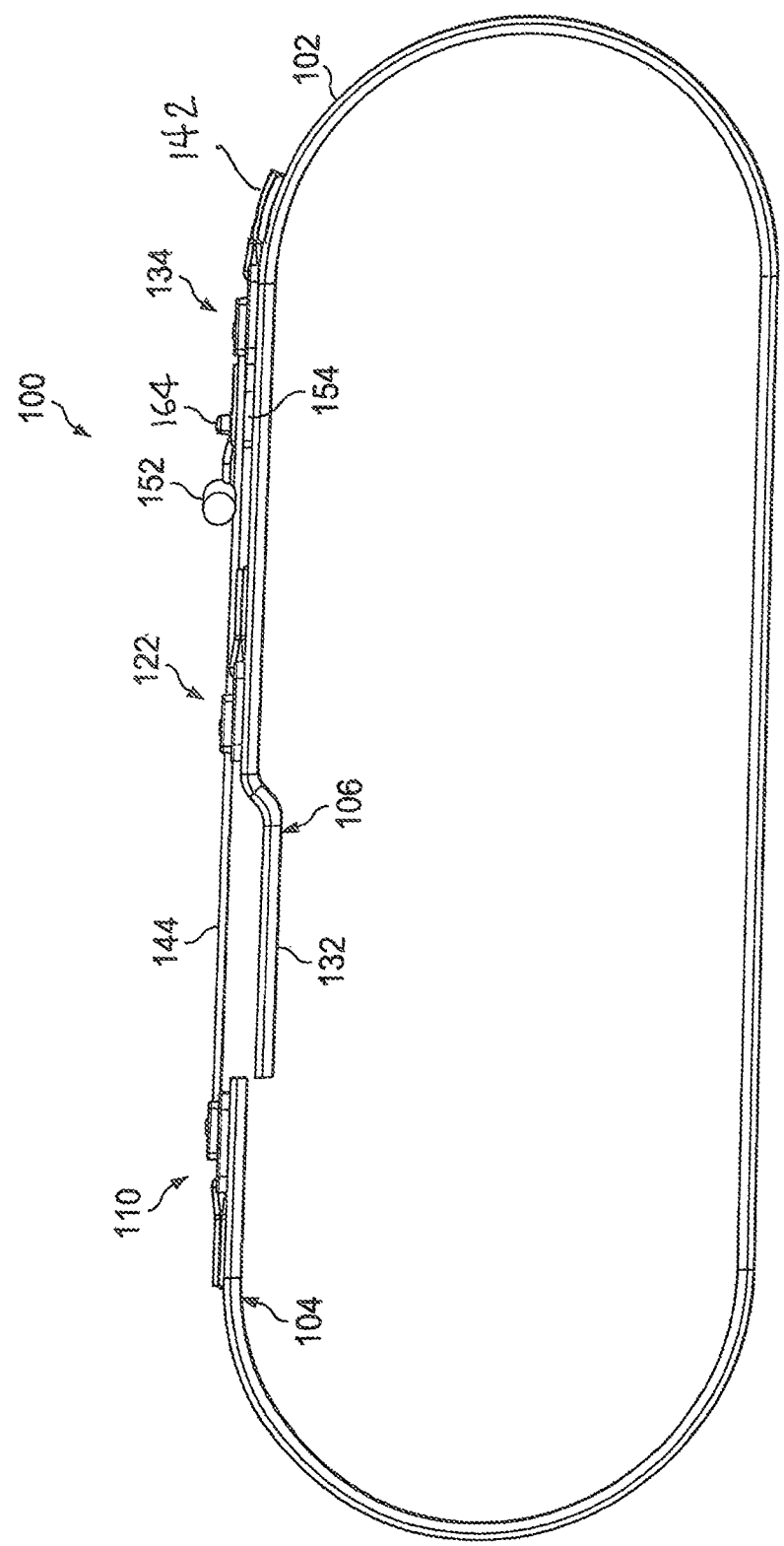

Referring again to FIG. 1, and now also to FIGS. 3A and 3B, a top view and side view of the compression belt 100 are shown to provide further details. A first pulley bank 110 is affixed to be first end portion 104. The first pulley bank 110 includes at least two pulleys 112 (see FIG. 3A) rotatably mounted on axles 114 within a housing 116. In the illustrated embodiment, the pulleys 112 of the first pulley bank 110 are arranged along a line 111 perpendicular to the centerline 108 of the belt body 102. In other embodiments, the pulleys 112 of the first pulley bank 110 may be arranged differently.

The first pulley bank 110 may be permanently affixed to the first end portion 104 of the belt body 102 in some embodiments, and releasably (i.e., removably or repositionably) affixed to the belt body in other embodiments. In the illustrated embodiment, the first pulley bank 110 is releasably affixed to the first end portion 104 by a flexible anchor strap 118 that is connected through a slot formed in the pulley housing 116. A quantity of hook-type fastening material is provided on the underside of the flexible anchor strap 118, and this hook-type material is used to engage loop-type fastening material provided in a fastening area 120 disposed on the first end portion 104. In this way, the compression belt 100 can be adjusted to size by choosing exactly where the flexible anchor strap 118 is attached within the fastening area 120. It is preferred to use loop-type fastening material on the surface of the belt body 102, since it has a softer feel than hook-type fastening material; however, the positions of the hook-type and loop-type fastening materials may be interchanged in other embodiments. In still other embodiments, other types of releasable fastening materials or devices may be used for releasably connecting the first pulley bank 110 to the belt body. In alternative embodiments, in which the first pulley bank 110 is permanently affixed to the first end portion 104, the flexible anchor strap 118 may be stitched, glued, riveted or otherwise connected to the belt body 102. In still other alternative embodiments, the pulley bank housing 116 may be stitched, glued or otherwise permanently attached directly to the belt body 102 without the use of the flexible anchor strap 118.

Referring still to FIGS. 1, 3A and 3B, the compression belt 100 further includes a second pulley bank 122 affixed to the second end portion 106. The second pulley bank 122 includes at least two pulleys 124 (see FIG. 3A) rotatably mounted on axles 126 within a housing 128. In the illustrated embodiment, the pulleys 124 of the second pulley bank 122 are arranged along a line 123 perpendicular to the centerline 108 of the belt body 102. In other embodiments, the pulleys 124 of the second pulley bank 122 may be arranged differently.

Similar to the first pulley bank 110, the second pulley bank 122 may be permanently affixed to the second end portion 106 of the belt body 102 in some embodiments, and releasably affixed to the belt body in other embodiments. However, in the illustrated embodiment, the second pulley bank 122 is permanently affixed to the second end portion 106 by a flexible anchor strap 130 that is connected through a slot formed in the pulley housing 128. The flexible anchor strap 130 is stitched to the belt body 102 in this embodiment, however in other embodiments gluing or other permanent affixing methods may be used. In alternative embodiments, the second pulley bank may be releasably fixed to the second end portion 106 as previously discussed in connection with the first pulley bank 110.

It will be appreciated that, while the second pulley bank 122 is affixed to the second end portion 106, the second pulley bank is not necessarily affixed at the extreme distal end of the belt body 102. In some embodiments, such as the one illustrated in FIG. 1, the second end portion 106 may include a free end section 132 at its extreme distal end. The free end section 132 may be tucked under the first end portion 104 when the belt body is positioned around the patient's body so that the first end portion "rides" on top of the free end section to reduce "pinching" or "bunching" when the compression belt is activated.

Referring still further to FIGS. 1, 3A and 3B, the compression belt 100 further includes a third pulley bank 134 affixed to the belt body 102 at a fixed distance, D1, from the second pulley bank 122. In some embodiments, the distance D1 may be about 6.0 inches. The third pulley bank 134 includes at least two pulleys 136 (see FIG. 3A) rotatably mounted on axles 138 within a housing 140. In the illustrated embodiment, the pulleys 136 of the third pulley bank 134 are arranged along a line 135 perpendicular to the centerline 108 of the belt body 102. In other embodiments, the pulleys 136 of the third pulley bank 134 may be arranged differently. As with the first two pulley banks, the third pulley bank 134 may be permanently affixed to the belt body 102 in some embodiments, and releasably affixed to the belt body in other embodiments. In the illustrated embodiment, the third pulley bank 134 is permanently affixed to the belt body 102 by a flexible anchor strap 142 that is connected through a slot formed in the pulley housing 140. The flexible anchor strap 142 is stitched to the belt body 102 in this embodiment, however in other embodiments gluing or other permanent affixing methods may be used. In alternative embodiments, the third pulley bank may be releasably fixed to the belt body 102, as previously discussed in connection with the first pulley bank 110 and the second pulley bank 122.

A flexible cord 144 interconnects the first, second and third pulley banks 110, 122, 134, the flexible cord having a first cord portion 146 extending between the pulleys 112, 124 of the first and second pulley banks 110, 122 in alternation. A second cord portion 148 is connected to the first cord portion 146 and extends between the pulleys 112, 136 of the first and third pulley banks 110, 134. A third cord portion 150 is connected at a first end to the second cord portion 148, and extends away from the third pulley bank 136.

The interconnection of the various portions 146, 148 and 150 of the flexible cord 144 through the respective pulleys 112, 124 and 136 of the three pulley banks 110, 122 and 134 creates a mechanical advantage mechanism substantially similar to a block and tackle. A handle 152 is connected to the second end of the third cord portion 150. Withdrawing the third cord portion 150 from the third pulley bank 134 by pulling the handle 152 away from the third pulley bank causes a shortening of the first cord portion 146 (i.e., the cord portion interconnected between the first pulley bank 110 and the second pulley bank 122) such that the distance D2 (see FIG. 3A) between the first and second pulley banks is reduced. This causes the belt body 102 to contract around the patient's body, applying circumferential compression to the portion of the patient's body underneath the compression belt 100. In other words, when the patient or technician pulls out on the handle 152 the flexible cord 144 runs through the block and tackle formed by the first second and third pulley banks 110, 122 and 134, and tightens the compression belt by moving the first and second pulley banks 110, 122 closer together (i.e., distance D2 is reduced). However, the distance D1 between the second and third pulley banks 122, 134 does not change when the handle 152 is pulled. In the illustrated embodiment, the handle 152 is an elongated, slightly curved cylinder forming a "T-shape" across the end of the third cord portion 150, and which is easy to grasp with one hand. In other embodiments, the handle 152 may have other shapes including, but not limited to, a D-ring style pull ring (see FIG. 2), with or without finger grooves, a ball, a ring or a heart-shaped pendant.

In preferred embodiments, the compression belt 100 further includes a selectively releasable one-way cord lock mechanism 154 connected to the belt body 102. The cord lock mechanism 154 includes a frame 156 defining a cord passage through which the third cord portion 150 is routed after leaving the third pulley bank 134. The cord lock mechanism 154 further includes a locking member 158 mounted in the frame 156 and movable between a locked position and a released position. A release member 160 is connected to the locking member 158 for moving the locking member between the locked position and a released position. Preferably, the release member 160 projects upwards from the cord lock mechanism 154 so that it is easily located by touch alone (i.e., without the patient or technician needing to see it).

In the illustrated embodiment of FIGS. 1, 3A and 3B, the cord lock mechanism 154 is connected directly to the housing 140 of the third pulley bank 134 such that the third cord portion 150 passes directly from the third pulley bank into the cord passage of the frame 156. In other embodiments, the cord lock mechanism 154 may be mounted directly to the belt body 102 or to another component of the belt 100. Further in the illustrated embodiment, the locking member 158 of the cord lock mechanism 154 comprises a toothed wheel which is mounted in a wedge-shaped slot 162 formed in the frame 156. The toothed wheel 158 can move laterally in the slot 162 to wedge the flexible cord 144 against the frame 156 in the locked position and to release the flexible cord so it can pass through the frame when in the unlocked position. Further still in the illustrated embodiment, the release member 160 includes a curved release handle 164 projecting from the upper surface of the frame 156. The curved release handle 164 assists the patient or technician in locating and activating the release member 160 in order to release the compression of the belt 100.

As it passes through the frame 156 of the locking mechanism 154, the third cord portion 150 is routed against the locking member 158 so as to bias the locking member toward the locked position. In the absence of external forces (such as activation of the release member 160), the biasing of the locking member 158 by the third cord portion 150 maintains the locking member in the locked position. The locking member 158, when in either of the locked position or the released position, allows withdrawal (i.e., pulling out) of the third cord portion 150 from the third pulley bank 134 to tighten the compression belt 100 and compress the selected portion of the patient's body. However, the locking member 158, when in the locked position, prevents the third cord portion 150 from retracting into the third pulley bank 134, thereby maintaining compression of the selected portion of the patient's body even if the patient or technician stops pulling on the handle 152. Thus, compression is maintained with "no hands required", i.e., in case the patient needs both hand for holding a walker, etc. or the technician is busy with other tasks. The locking member, 158, when in the released position, allows the third cord portion 150 to retract into the third pulley bank 134 to discontinue compression of the selected portion of the patient's body. Thus, by simply pulling the handle 152 with one hand, the patient or technician can selectively produce circumferential compression of the selected body portion by the belt 100, and the circumferential compression is maintained even if the patient or technician quits pulling on the handle. Subsequently, by pushing the release member 160 (or release handle 164) to the released position, the patient or technician can release any compression held by the belt 100.

Figure 4:
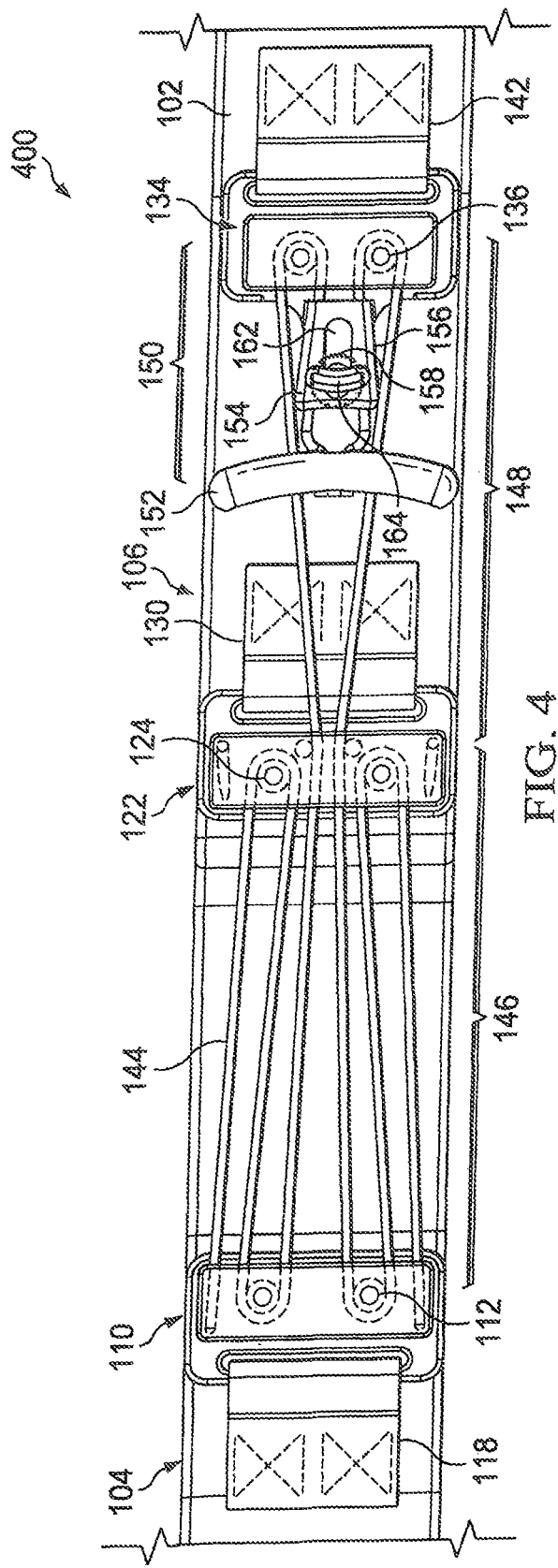
FIG. 4 is an enlarged partial top view of a compression belt similar to the compression belt of FIG. 1, in accordance with another embodiment.

Referring now to FIG. 4, there is illustrated an enlarged partial top view of a compression belt 400 similar to the compression belt 100 of FIG. 1, in accordance with another embodiment. The compression belt 400 is substantially similar in most respects to the belt 100 previously described, and therefore common reference numbers are used for similar elements. As is clearly shown in FIG. 4, the compression belt 400 does not have a fastening area 120 formed of attachment material 109 for releasably securing the flexible anchor strap 118. Instead, the flexible anchor strap 118 of the compression belt 400 is permanently affixed to the first end portion 104 of the belt body 102 via stitching.

Referring now again to FIG. 2, the compression belt 200 is substantially similar in many respects to the belt 100 previously described such a common reference numbers are used for similar elements. However, some aspects of compression belt 200 are changed to accommodate the different application. For example, in a preferred embodiment of the compression belt 200, the belt body 202 may have an overall width (measured perpendicular to the centerline 108) of about 5.0 inches and a length (measured along the centerline) of about 60 inches.

Figure 5A:
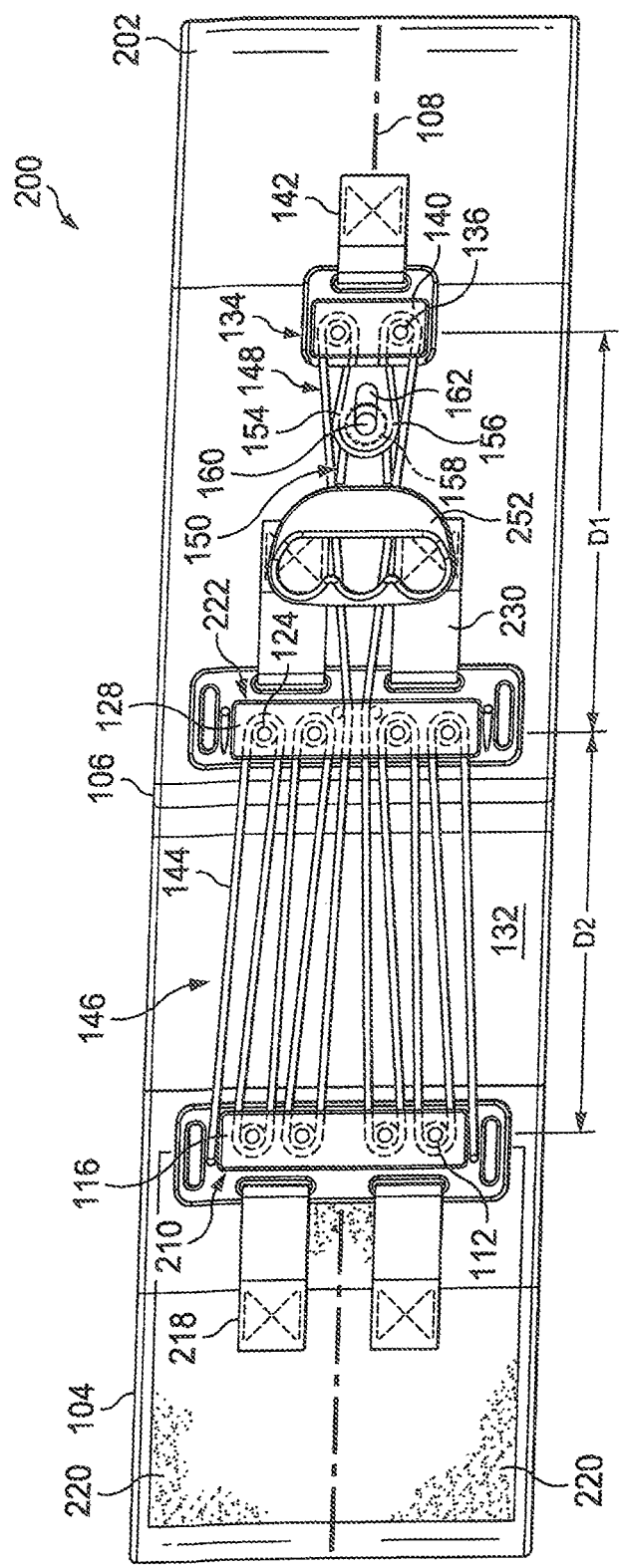
FIGS. 5A and 5B are, respectively, a top view and a side view of the compression belt of FIG. 2.
Figure 5B:
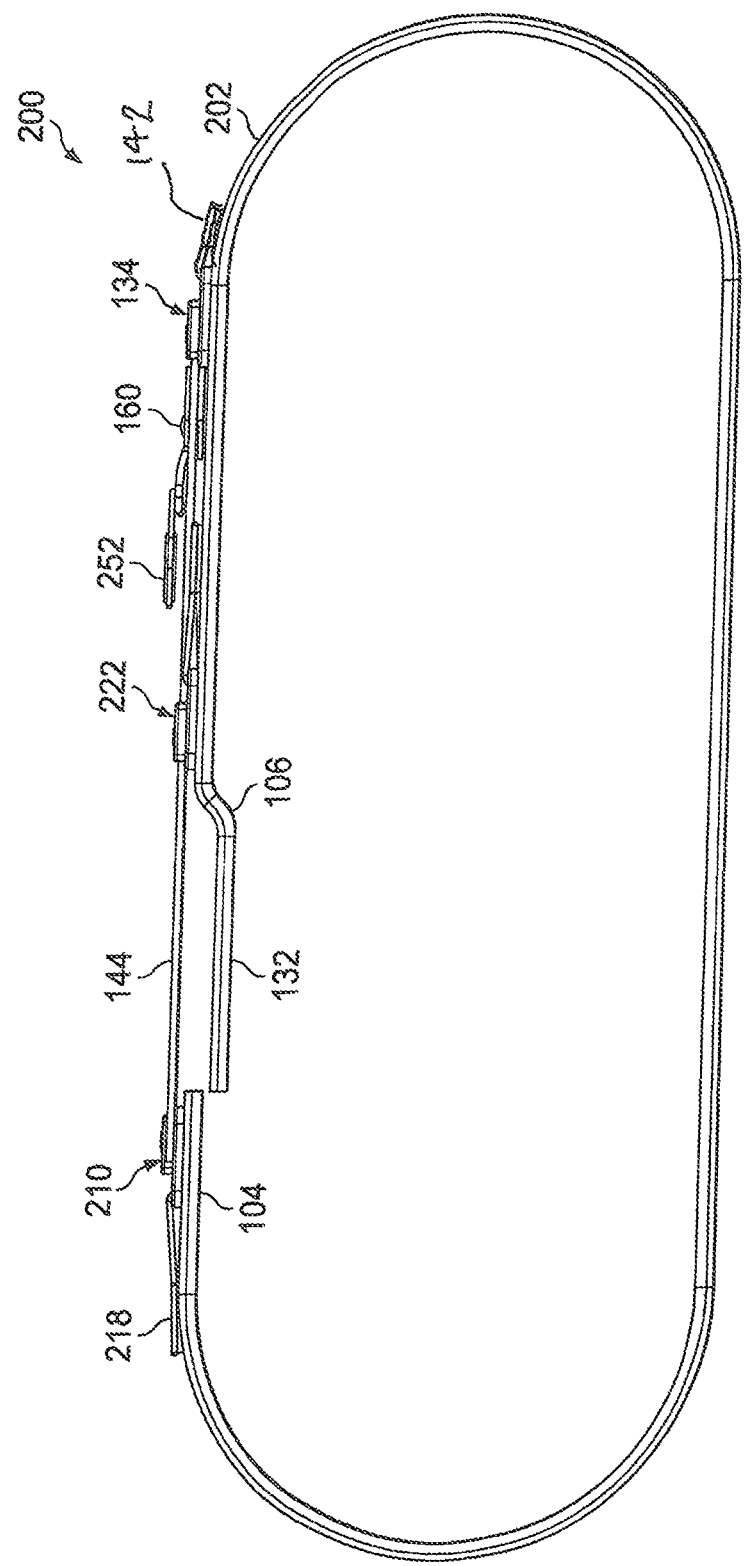

Referring still to FIG. 2, and also to FIGS. 5A and 5B, a top view and side view of the compression belt 200 are shown to provide further details. In particular, in compression belt 200, the first pulley bank 210 includes four pulleys 112 (see FIG. 5A) mounted on axles 114 within a housing 116. In the illustrated embodiment, the pulleys 112 of the first pulley bank 210 are arranged along a line 211 perpendicular to the centerline 108 of the belt body 202, however, in other embodiments, the pulleys 112 of the first pulley bank 210 may be arranged differently. Similarly, a compression belt 200 the second pulley bank 222 also includes four pulleys 124 (see FIG. 5A) mounted on axles 126 within a housing 128. In the illustrated embodiment, the pulleys 124 of the second pulley bank 222 are arranged along a line 223 perpendicular to the centerline of the belt body 202, however, in other embodiments, the pulleys 124 of the second pulley bank may be arranged differently. The third pulley bank 134 of the compression belt 200 may contain only two pulleys 136 as in the compression belt 100. The four-pulley pulley banks 210 and 222 interconnected by flexible cord 144 and also connected to the two-pulley pulley bank 134 results in a block-and-tackle mechanism for the compression belt 200 with a mechanical advantage of about 5:1, which is greater than the 3:1 mechanical advantage block-and-tackle mechanism of the compression belt 100.

It will further be appreciated that the pulley banks 210 and 222 are affixed to the belt body 202 using dual flexible anchor straps 218 and 230, respectively. In the illustrated embodiment of FIGS. 2, 5A and 5B, the flexible anchor straps 218 are releasably affixed to a fastening area 220 disposed on the first end portion 104 and the flexible anchor straps 230 are permanently affixed to the second free end portion 106. In addition, in this embodiment, the flexible anchor strap 142 on the third pulley bank 134 is permanently attached to the belt body 202. In other embodiments, the various anchor straps 218, 230, 142 may be attached or affixed in alternative manners as described in connection with compression belt 100.

In the illustrated embodiment of compression belt 200, a handle 252 having a D-ring style with finger grips is provided. The one way cord release mechanism 154 has a different external configuration, but functions in the same manner as the cord release mechanism previously described.

Figure 6:
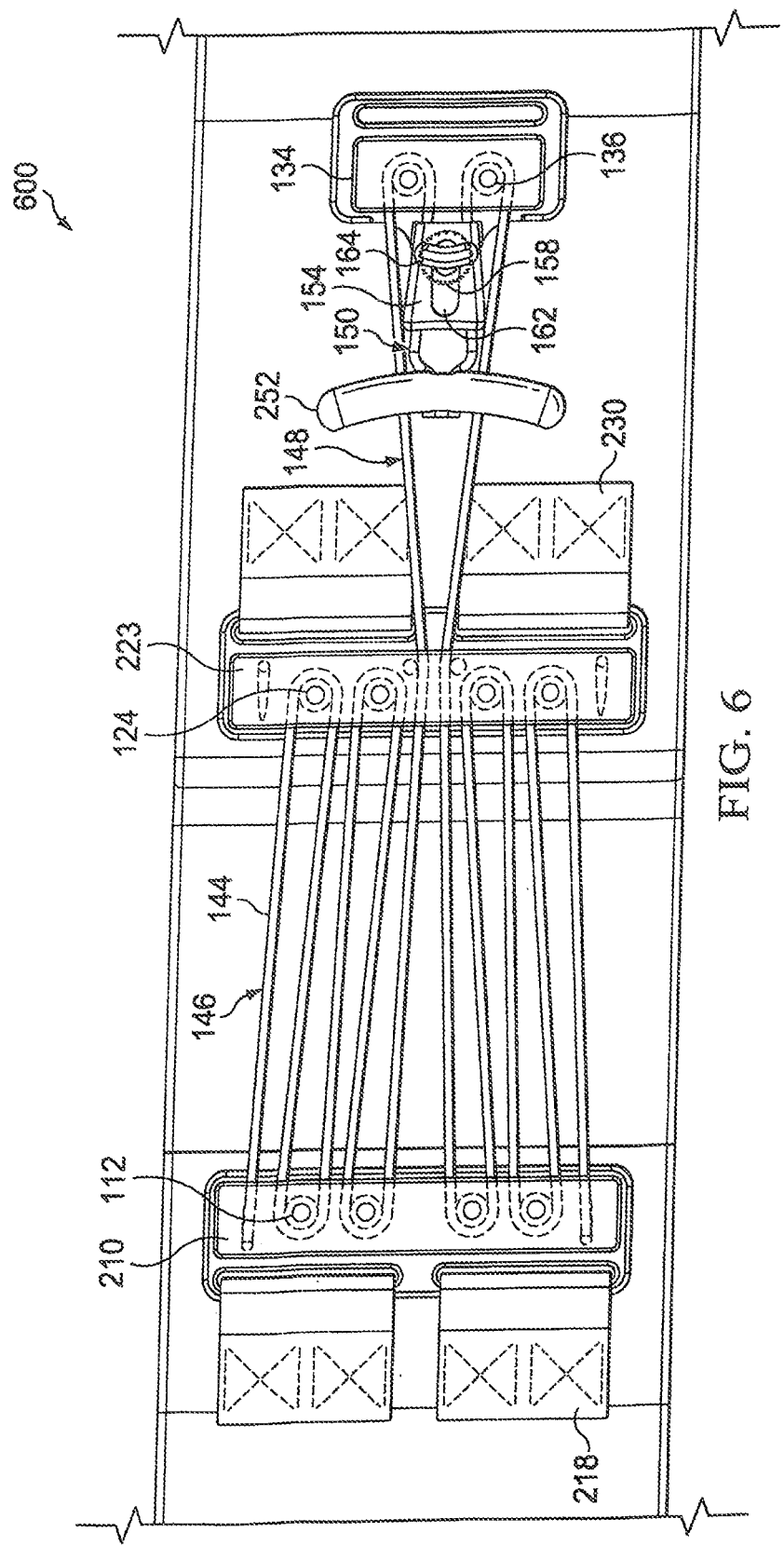
FIG. 6 is an enlarged partial top view of a compression belt similar to the compression belt of FIG. 2, in accordance with another embodiment.

Referring now to FIG. 6, there is illustrated an enlarged partial top view of a compression belt 600 similar to the compression belt 200 of FIGS. 2, 5A and 5B, in accordance with another embodiment. The compression belt 600 is substantially similar in most respects to the belt 200 previously described, and therefore common reference numbers are used for similar elements. Some of the changes include a new configuration for the pull handle 252, for the release handle 164 and for the configuration of the various pulley banks 210, 222 and 134.

As previously described, the compression belts 100, 200, 400 and 600 can be worn by the user after chest surgery. The selected belt is typically worn with the belt body 102 encircling the user's chest such that the underside of the belt body lies uniformly against the user's body. When the user anticipates movement or coughing, the handle 152, 252 is pulled to draw the flexible cord 144 through the pulley banks 110, 122 and 134, pulling the first and second end portions 104, 106 towards one another, causing uniform circumferential tightening of the belt body 102 around the user's chest, which reduces the user's discomfort associated with movement or coughing. After the movement or cough has ended, the user can release the handle 152, 252 and/or the cord lock mechanism 154, and the belt body 102 can release the tightening and return to its original position.

Figure 7A:
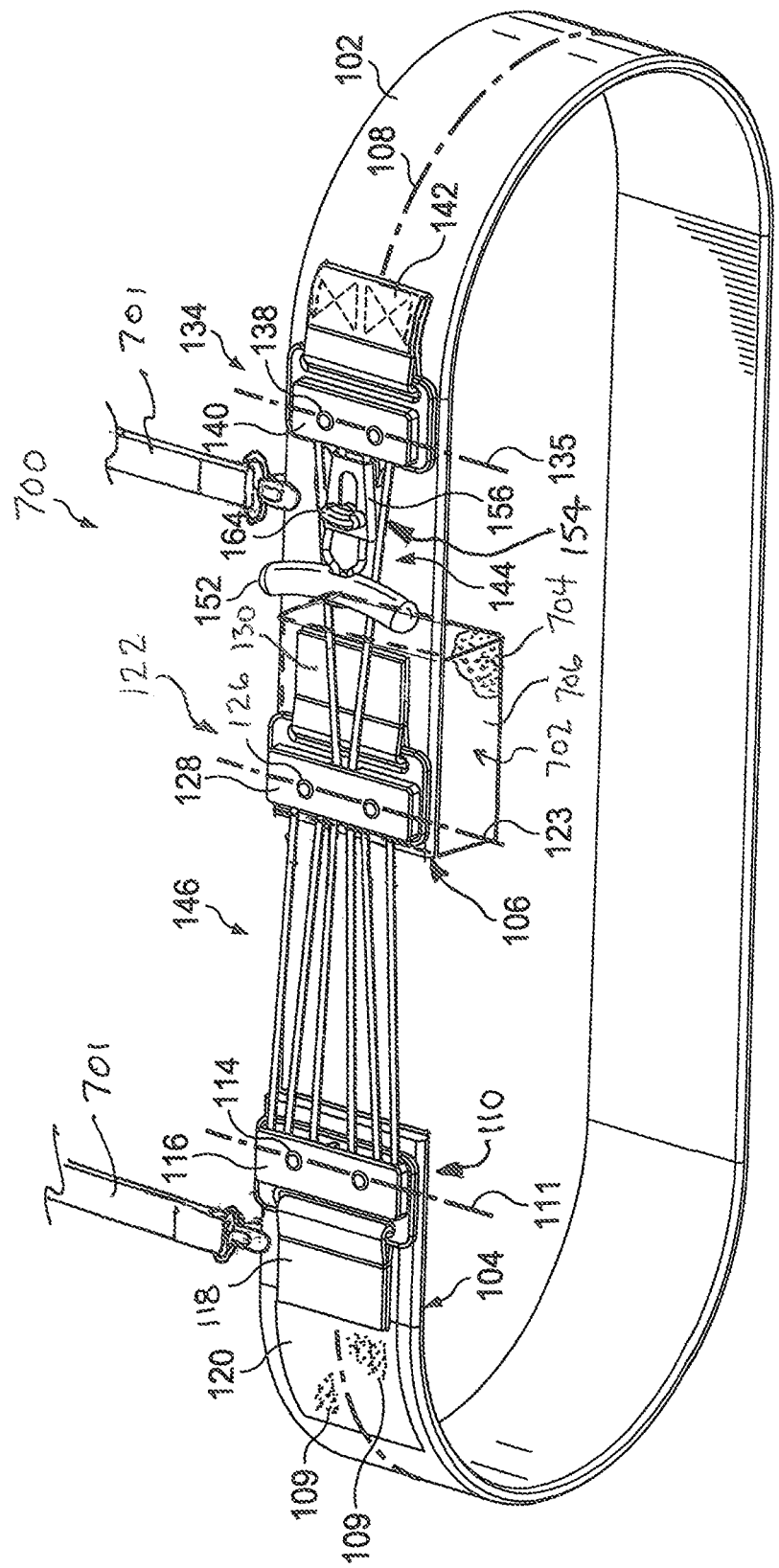
Figure 7B:
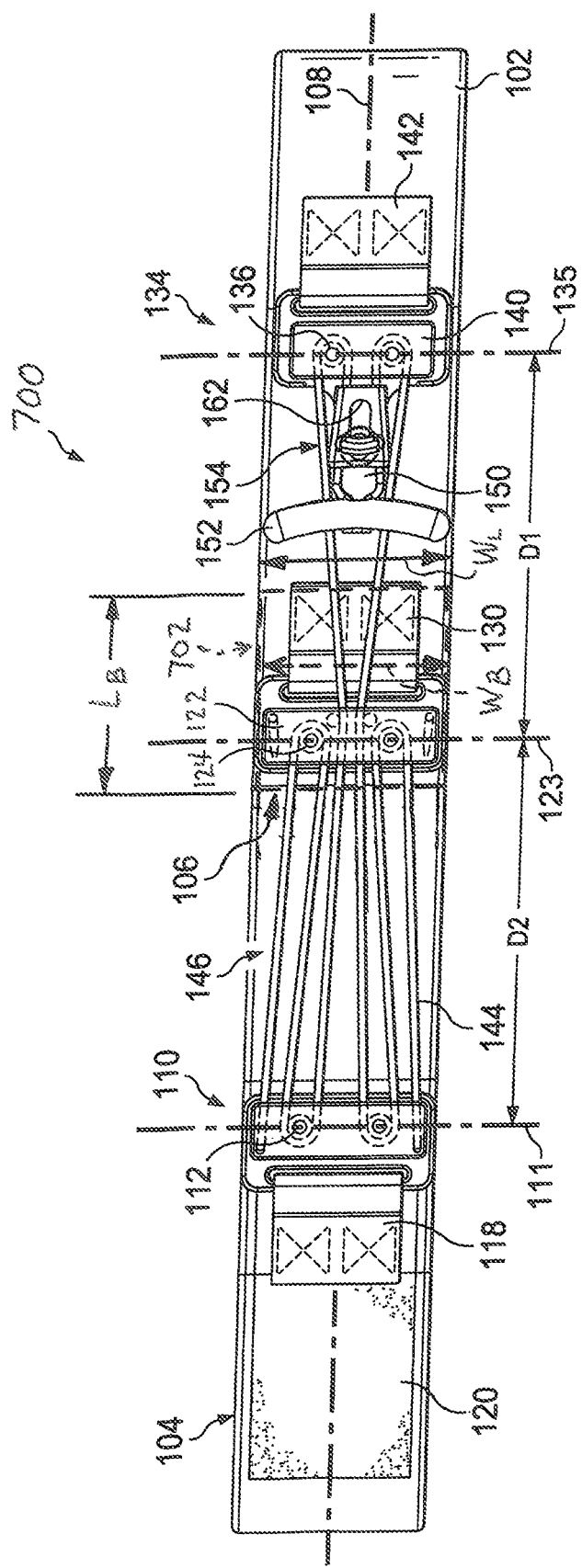
Figure 7C:
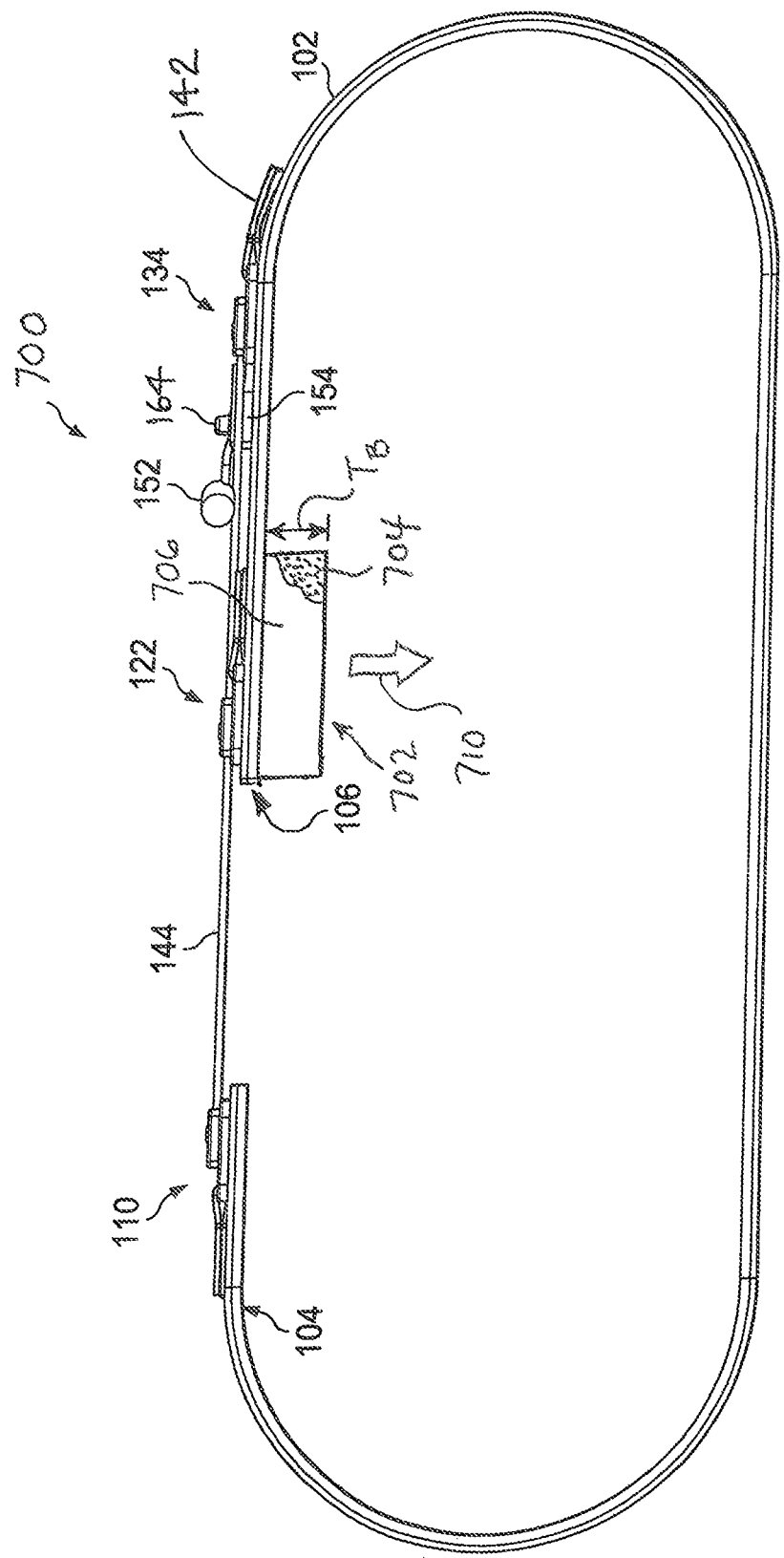

Referring now to FIGS. 7A-7C, there is illustrated a compression belt 700 in accordance with another aspect. Except as otherwise described, the compression belt 700 is substantially similar in many respects to the belt 100 previously described, therefore common reference numbers are used for similar elements. The belt body 102 is adapted to be wrapped circumferentially around a selected portion of the patient's body. In some embodiments, the belt body 102 is adapted to be wrapped around the patient's chest portion with the free end portions 104 and 106 disposed near the patient's sternum. In some embodiments, the belt 700 further includes one or more suspender straps 701 that can be draped over the patient's shoulders and attached to the belt body 102 on opposite sides of the patient's body to maintain the belt body at a desired level (e.g., with centerline 108 even with the patient's sternum) even when the belt is worn loosely (i.e., uncompressed) on the body. In some embodiments, the free end section 132 (e.g., FIG. 1) can be substantially shorter such that the free end portion 106 ends near the second pulley bank 122. The compression belt 700 includes a thick, compressible buffer 702 attached to the underside of the belt body 102 (the underside being the side facing inward toward the user when worn). In the illustrated embodiment, the buffer 702 is attached to the underside of the second end portion 106 of the belt body 102 and below-adjacent to the second pulley bank 122 and/or flexible anchor strap 130. In other embodiments, the buffer 702 can be attached to other portions of the belt body 102. The buffer 702 can be permanently attached to the belt body 102 or can be releasably attached, e.g., through the use of hook and loop fastener material.

The buffer 702 can be formed of a flexible, highly compressible material 704. The compressible material 704 can be used alone (i.e., uncovered) or covered by a protective or decorative jacket 706. The embodiment of FIGS. 7A-7C includes a jacket 706, and in FIGS. 7A and 7C, a portion of the jacket is shown broken away for purposes of illustration to show the underlying compressible material 704. In some embodiments, the compressible material 704 of the buffer 702 can be, but is not limited to, a rubber foam, a polyurethane plastic foam, a urethane plastic foam or a polyether plastic foam, used either alone or with the jacket 706. In some embodiments, the compressible material 704 of the buffer 702 has a density in the range from 1.1 pounds per cubic foot to 1.5 pounds per cubic foot and an indentation load deflection ("ILD") (an industry-wide measure of firmness, also known as an indentation force deflection ("IFD")), in the range from 50 pounds to 80 pounds. In another embodiment, the compressible material 704 has a density of 1.3 pounds per cubic foot and an ILD of 70 pounds. In still another embodiment, the buffer 702 can include multiple layers of compressible materials 704 having different densities and/or ILD values. In a further embodiment, the compressible material 704 of the buffer 702 can be a fiber stuffing material filling the jacket 706, including, but not limited to, a polyester fiber stuffing (i.e., fiberfill or poly-fill).

The jacket 706 can be formed of a natural or synthetic fabric or a plastic film or a plastic layer. In some embodiments the jacket 706 is removable for cleaning or replacement. In other embodiments the jacket 706 is removable so that the user can choose from a plurality of different decorative jackets. In still other embodiments the jacket 706 is permanently sealed over to the compressible material 704 to prevent the ingress of fluids into the buffer 702.

Figure 8A:
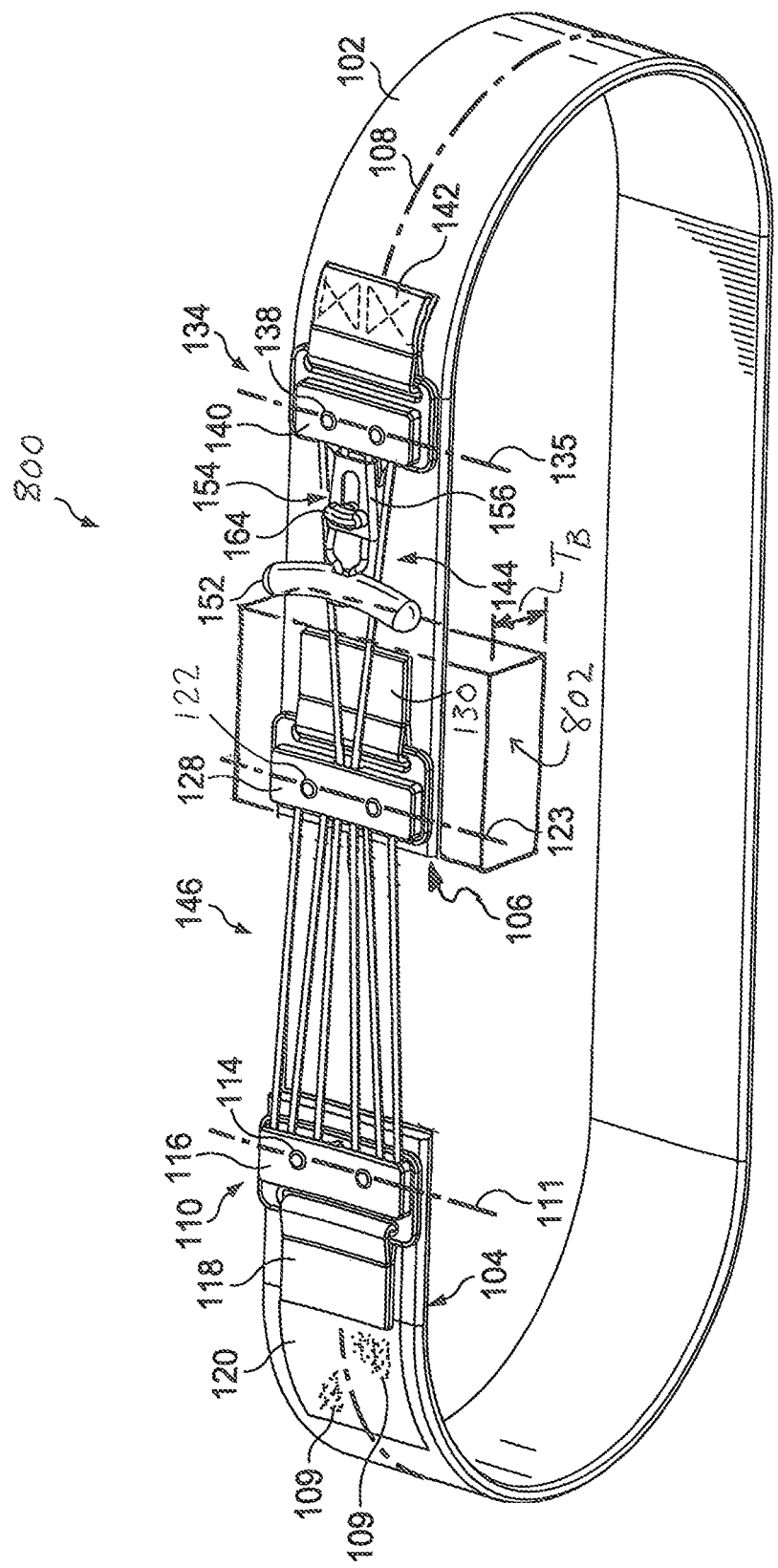

Referring now to FIGS. 7B and 7C, the dimensions of the buffer 702 can be specified, either in absolute terms or relative to the lateral width $W_L$ of the belt body 102, where $W_L$ is measured across the belt body in a direction perpendicular to the centerline 108. In particular, the buffer 702 can have a width $W_B$ measured in a direction parallel to the lateral width $W_L$ of the belt body 102, a length $L_B$ measured in a direction parallel to the centerline 108, and a thickness $T_B$ measured perpendicular to $W_B$ and $T_B$. In FIG. 7B, $W_B$ is indicated by a dashed line because the buffer 702, also shown in dashed line, lies completely behind the belt body 102. In the embodiment of FIGS. 7A-7C, the buffer 702 has a rectangular shape with width $W_B=1.0\times W_L$, length $L_B=1.1\times W_L$ and thickness $T_B=0.35\times W_L$. Thus, in one such embodiment having a belt body 102 with a lateral width $W_L=4.0$ inches, the buffer 702 can have a width $W_B=4.0$ inches, a length $L_B=4.4$ inches and a thickness $T_B=1.4$ inches. In another such embodiment having a belt body 102 with a lateral width $W_L=5.0$ inches, the buffer 702 can have a width $W_B=5.0$ inches, a length $L_B=5.5$ inches and a thickness $T_B=1.75$ inches. In these embodiments, the buffer is termed a "full-width" buffer because the buffer width $W_B$ is equal to the belt body lateral width $W_L$. In an alternative full width buffer embodiment, the buffer 702 has a square shape with width $W_B=1.0\times W_L$, length $L_B=1.0\times W_L$ and thickness $T_B$ in the range from 0.25 to $0.40\times W_L$. Thus, in one such alternative embodiment having a belt body 102 with a lateral width $W_L=4.0$ inches, the buffer 702 can have a width $W_B=4.0$ inches, a length $L_B=4.0$ inches and a thickness $T_B$ in the range from 1.0 inches to 1.6 inches. In another such alternative embodiment having a belt body 102 with a lateral width $W_L=5.0$ inches, the buffer 702 can have a width $W_B=5.0$ inches, a length $L_B=5.0$ inches and a thickness $T_B$ in the range from 1.25 inches to 2.00 inches. Other embodiments may have differences in one or more of these dimensions. For example, in some further embodiments, the thickness $T_B$ of the buffer 702 can be within the range from 1.0 inches to 2.0 inches, regardless of the other dimensions. In still further embodiments, the thickness $T_B$ can be within the range from 1.5 inches to 1.75 inches Referring now to FIGS. 8A and 8B, there is illustrated a compression belt 800 in accordance with another aspect. Except as otherwise described, the compression belt 800 is substantially similar in many respects to the belt 700 previously described, therefore common reference numbers are used for similar elements. Suspenders 701 can be included in some embodiments, but are not shown in the illustrated embodiment. The compression belt 800 includes a buffer 802 similar to the buffer 702 previously described, except the buffer 802 is an "over width" buffer because the buffer width $W_B$ exceeds the belt body lateral width $W_L$. In this case, the side view of the compression belt 800 will be substantially identical to the side view of belt 700 shown in FIG. 7C. In the embodiment of FIGS. 8A and 8B, the buffer 802 can have a rectangular shape with width $W_B=1.4\times W_L$, length $L_B=1.1\times W_L$ and thickness $T_B=0.35\times W_L$. Thus, in one embodiment having a belt body 102 with a lateral width $W_L=4.0$ inches, the buffer 802 can have a width $W_B=5.6$ inches, a length $L_B=4.4$ inches and a thickness $T_B=1.4$ inches. In another embodiment having a belt body 102 with a lateral width $W_L=5.0$ inches, the buffer 702 can have a width $W_B=7.0$ inches, a length $L_B=5.5$ inches and a thickness $T_B=1.75$ inches. Other embodiments may have differences in one or more of these dimensions. For example, in some further embodiments, the thickness $T_B$ of the buffer 802 can be within the range from 1.0 inches to 2.0 inches, regardless of the other dimensions. In still further embodiments, the thickness $T_B$ can be within the range from 1.5 inches to 1.75 inches The compression belts 700 and 800 having respective buffers 702, 802 are typically worn with the belt body 102 encircling the user's chest and the buffer 702, 802 positioned inside the belt body against the user's chest, preferably directly over the user's sternum. When worn in this manner, the inner surface of the belt body 102 lies directly against the user's back and sides, but due to the thickness of the buffer 702, 802, the inner surface of the belt body remains spaced-apart from the user's body behind the buffer and for a short distance adjacent to each side of the buffer. As with the previously described compression belts, e.g., belt 100, when the user anticipates movement or coughing, the handle 152 is pulled to draw the flexible cord 144 through the pulley banks 110, 122 and 134, pulling the first and second end portions 104, 106 towards one another. However, due to the stand-off distance between the user's chest and the belt body 102 in the vicinity of the buffer 702, 802, pulling the end portions 104 and 106 towards one another produces not only circumferential tightening, but also compresses the buffer inward against the user's chest. This compression of the buffer 702, 802 against the user's chest, produces localized pressure beneath the buffer applied in an inward direction, i.e., directly toward the chest or sternum. This direct inward pressure provide by the buffer 702, 802 can greatly enhance the therapeutic (i.e., discomfort-reducing) effects of the belt 700, 800 compared to circumferential tightening alone.

Referring now to FIGS. 9A-9C, there are illustrated schematic force and pressure diagrams of a compression belt, e.g., belt 700, having a full-width pressure-enhancing buffer 702. FIG. 9A shows a cross-section of the belt body 102 and the attached buffer 702 prior to compression of the flexible material 704 (i.e., the thickness of the buffer is 100% of $T_B$). Arrows 902 schematically represent the downward forces that will be applied to the buffer 702 by tensioning the belt body 102 during activation of the pulley system; however, negligible downward pressure is transmitted to the user's chest in FIG. 9A because the flexible material 704 is not yet compressed.

FIG. 9B illustrates that the forces 902 from the belt body 102 have now compressed the flexible material 704 of the buffer 702 to approximately 50% of the original thickness, i.e., 50% $T_B$. Arrows 904 schematically represent the resultant forces transmitted from the buffer 702 to the user's chest, which result from compression of the flexible material 704.

FIG. 9C illustrates a schematic pressure profile resulting from the forces 904 of FIG. 9B applied to the user's chest, where P represents the value of pressure and X represents positions across the user's chest (moving in a line beginning a short distance below the belt 700, crossing the belt laterally, and ending a short distance above the belt). The pressure profile in FIG. 9C show that the pressure is uniformly applied beneath the full-width buffer 702. This results in a relatively average pressure (average force per unit area), but also results in a significant pressure discontinuities 906 at the edges of the buffer 702. A sub-width buffer (not shown), i.e., having $W_B$ less than $W_L$, will have a schematic pressure profile substantially similar to the full-width pressure profile of FIG. 9C; however, the average pressure would be proportionally higher.

Referring now to FIGS. 10A-10C, there are illustrated schematic force and pressure diagrams of a compression belt, e.g., belt 800, having an over-width pressure-enhancing buffer 802. FIG. 10A shows a cross-section of the belt body 102 and the attached buffer 802 prior to compression of the flexible material 704 (i.e., the thickness of the buffer is 100% of $T_B$). Since the buffer 802 is over-width, the buffer includes a central area 1003 disposed directly below the belt body 102 and "fringe" areas 1005 disposed on either side of the central area and not directly below the belt body. Arrows 1002 schematically represent the downward forces that will be applied to the buffer 802 by tensioning the belt body 102 during activation of the pulley system. Note that the forces 1002 will only be applied to the central area 1003 underlying the belt body 102, and negligible downward pressure is transmitted to the user's chest in FIG. 10A because the flexible material 704 is not yet compressed.

FIG. 10B illustrates that the forces 1002 from the belt body 102 have now compressed the flexible material 704 of the buffer 802 to approximately 50% of the original thickness, but only in the central area 1003 of the buffer directly under the belt body. The fringe areas 1005 of the buffer 802, i.e., those areas not lying directly below the belt body 102, remain relatively uncompressed in proportion to their distance from the edge of the belt body, with the outer edge of the flexible material being the least compressed. Arrows 1004 schematically represent the resultant forces transmitted from the buffer 802 to the user's chest, which result from compression of the flexible material 704. Since the degree of compression of the flexible material 704 in the fringe areas 1005 in FIG. 10B varies according to the distance from the edge of the belt body 102, the forces 1004 transmitted to the user by the fringe area of the buffer 802 also vary according to the distance from the edge of the belt body.

FIG. 10C illustrates a schematic pressure profile resulting from the forces 1004 of the over-width buffer 802 of FIG. 10B applied to the user's chest, where P represents the value of pressure and X represents positions across the user's chest (moving in a line beginning a short distance below the belt 700, crossing the belt laterally, and ending a short distance above the belt). The pressure profile in FIG. 10C show that the pressure is non-uniformly applied beneath the over-width buffer 802. The pressure in the central area 1003 is relatively uniform, but tapers from the uniform value towards zero in the fringe areas 1005. This results in a relatively lower average pressure compared to a full-width buffer 702, and also significant smaller pressure discontinuities 1006 at the edges of the buffer 802 compared to the full-width buffer. Thus, each type of buffer configuration provides a different pressure profile: A full-width (or sub-width) buffer 702 may be indicated where the user desires a "firm" pressure and is not discomforted by relatively larger pressure discontinuities 906, whereas an over-width buffer 802 may be indicated where the user prefers the well-graduated application of pressure with relatively lower pressure discontinuities 1006, which may be perceived as a "gentle" pressure.

Figure 11A:
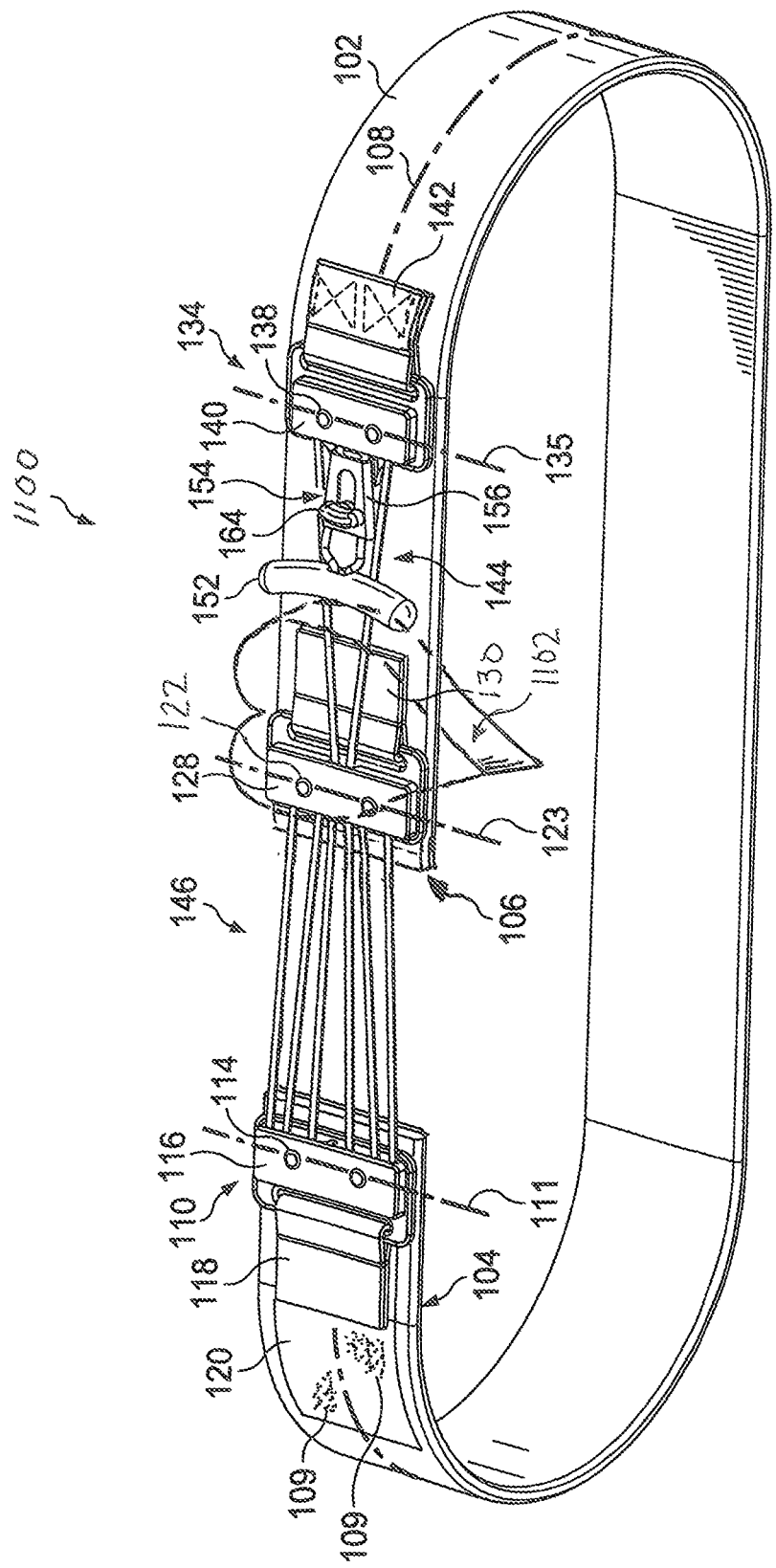
Figure 11B:
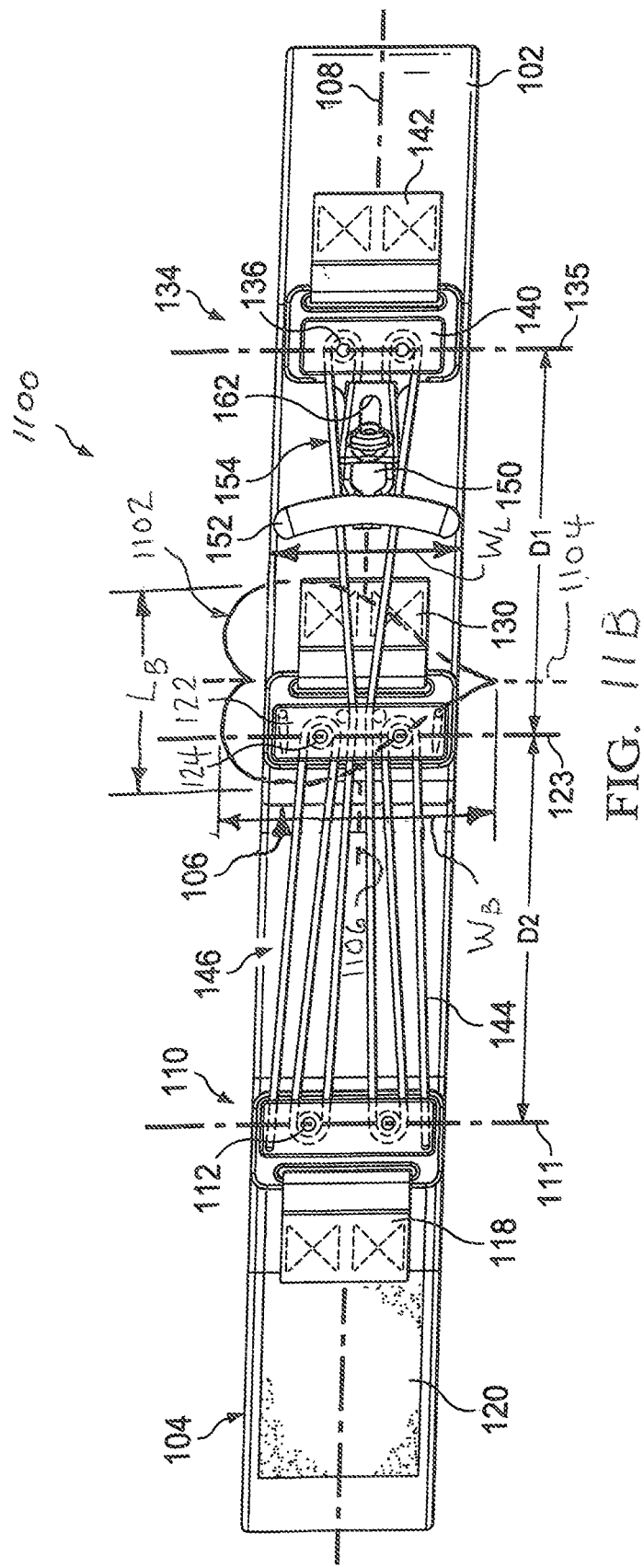
Figure 11C:
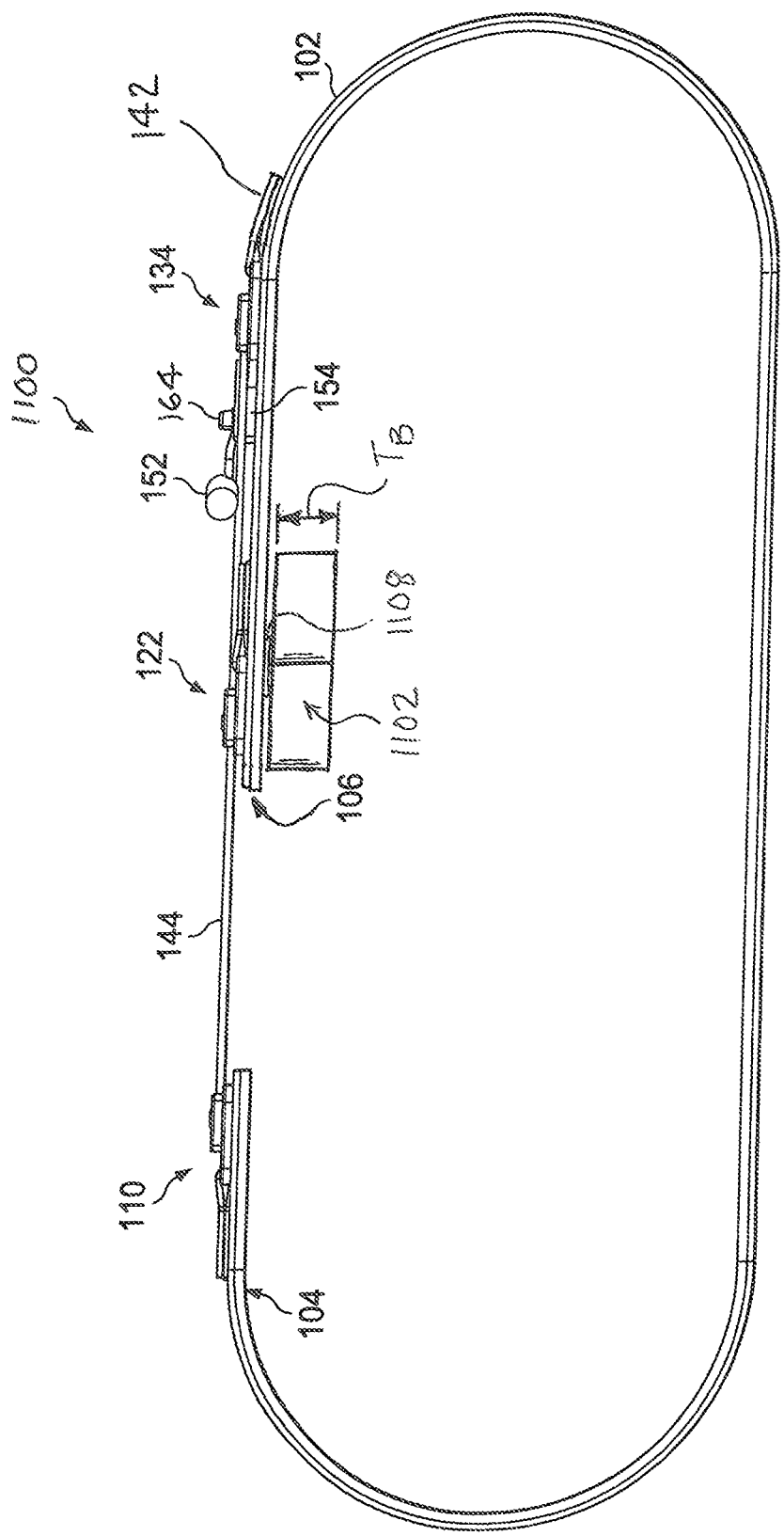

Referring now to FIGS. 11A-11C, there is illustrated a compression belt 1100 in accordance with yet another aspect. Except as otherwise described, the compression belt 1100 is substantially similar in many respects to the belt 800 with over-width buffer 802 previously described, therefore common reference numbers are used for similar elements. Suspenders 701 can be included in some embodiments, but are not shown in the illustrated embodiment. The compression belt 1100 includes a buffer 1102 similar to the buffer 802 previously described, except the buffer is non-symmetrical along at least one axis. In the illustrated embodiment, as best seen in FIG. 11B, the buffer 1102 is shaped like a stylized heart, which is symmetrical about a first centerline 1104 parallel to the width direction, but non-symmetrical about a second centerline 1106 parallel to the length direction. Since the heart-shaped buffer 1102 is over-width, the heart shape is at least partially visible from the front side of the belt body 102. The heart-shaped buffer 1102 can be formed of flexible material 704 with or without a protective jacket 706. As best seen in FIG. 11C, in the illustrated embodiment the buffer 1102 is removably attached to underside of the belt body 102 with hook and loop fastening material 1108, for example with Velcro® brand fastening material (one hook or loop portion being affixed to the belt body, and the complementary portion being affixed to the buffer); however, other removable or permanent attaching features can be used in other embodiments. In addition, in some embodiment, the heart-shaped buffer 1102 can be provided with a red exterior coloring to assist the user (especially elderly users) in seeing the location of the buffer for purposes of correctly placing it over their sternum. If the heart-shaped buffer 1102 does not include a jacket 706, the flexible material 704 can have a red exterior coloring by painting or dyeing the flexible material or by using a flexible material that is inherently red. If the heart-shaped buffer 1102 includes a jacket 706, the red exterior coloring can be provided by using red colored fabric or plastic for the jacket, or by painting or dyeing the material of the jacket.

In the embodiment of FIGS. 11A-11C, the heart-shaped buffer 1102 can have a width $W_B=1.4\times W_L$, length $L_B=1.1\times W_L$ and thickness $T_B=0.35\times W_L$. Thus, in one embodiment having a belt body 102 with a lateral width $W_L=4.0$ inches, the heart-shaped buffer 1102 can have a width $W_B=5.6$ inches, a length $L_B=4.4$ inches and a thickness $T_B=1.4$ inches. In another embodiment having a belt body 102 with a lateral width $W_L=5.0$ inches, the heart-shaped buffer 1102 can have a width $W_B=7.0$ inches, a length $L_B=5.5$ inches and a thickness $T_B=1.75$ inches. Other embodiments may have differences in one or more of these dimensions. For example, in some further embodiment, the thickness $T_B$ of the buffer 1102 can be within the range from 1.0 inches to 2.0 inches, regardless of the other dimensions. In still further embodiments, the thickness $T_B$ can be within the range from 1.5 inches to 1.75 inches Referring now to FIG. 12 there is illustrated a compression belt 1200 in accordance with a still further aspect. Except as otherwise described, the compression belt 1200 is substantially similar in many respects to the belts 100, 200, 400 and 600 previously described, therefore common reference numbers are used for similar elements. Suspenders 701 can be included in some embodiments, but are not shown in the illustrated embodiment. The compression belt 1200 has a belt body 102 that further includes at least one respiratory expansion panel 1202 that can stretch or elongate elastically in the centerline direction (i.e., the direction parallel to the belt centerline 108). In other words, when tension is applied to the respiratory expansion panel 1202, the panel can elongate or stretch in the centerline direction from an original length $L_O$ up to a maximum length $L_{Max}$, and when the tension is released, the panel can return to the original length $L_O$. Since the other portions of the belt body 102 (i.e., exclusive of the respiratory expansion panel 1202) can be made of substantially non-elastic materials, prolonged activation of a compression belt that does not include a respiratory expansion panel can potentially inhibit deep, natural breathing of the user. Inclusion of one or more respiratory expansion panels 1202 allows prolonged tensioning of the belt 1200 (e.g., to provide rib stabilization) while also ensuring that belt will have sufficient elasticity to allow deep, natural breathing by the user.

Figure 12:
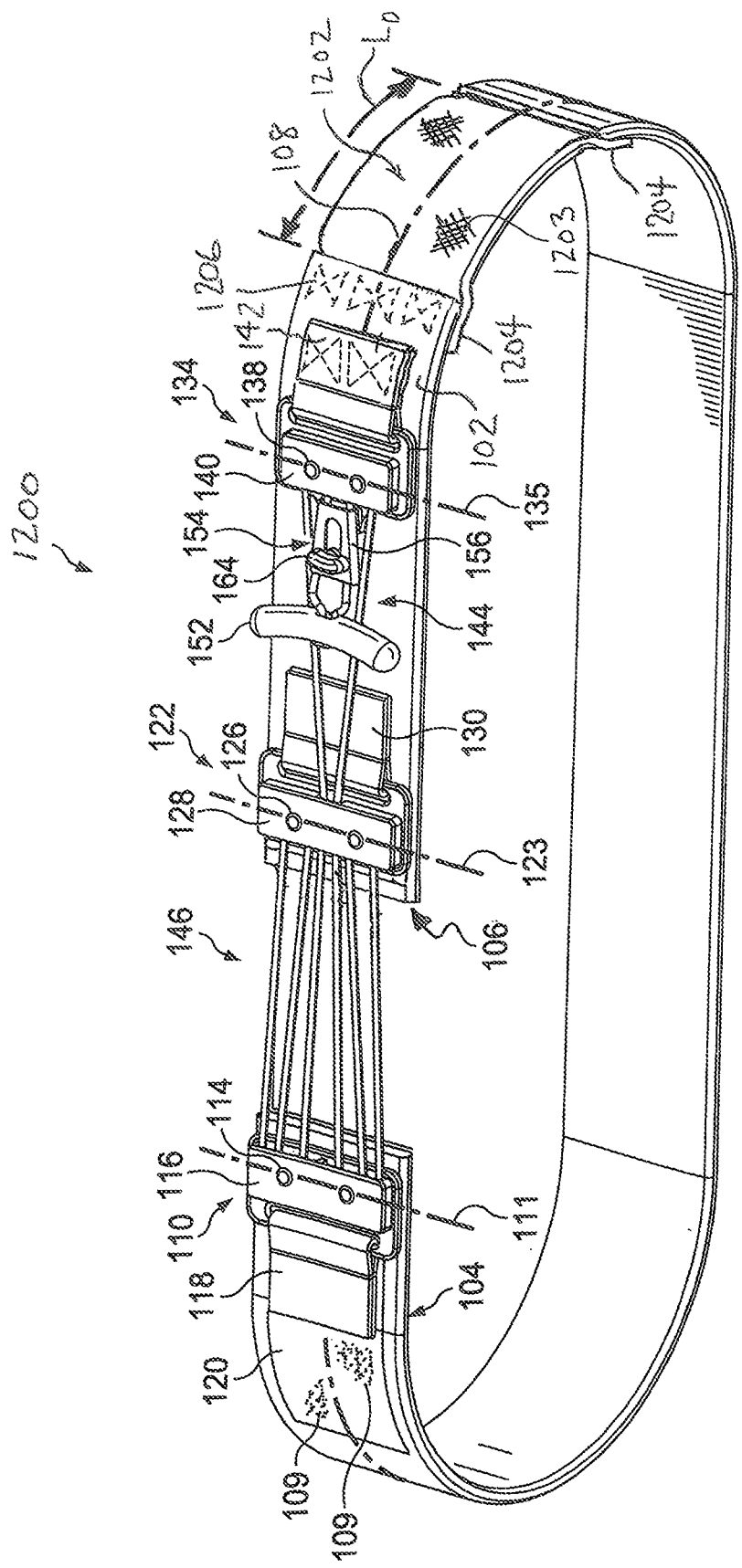
FIG. 12 shows a perspective view of a compression belt for selective temporary chest compression with respiratory expansion panel in accordance with a further aspect.

In the embodiment of FIG. 12, the respiratory expansion panel 1202 is a section of elastic fabric 1203 that spans the full width of the belt body 102 and is joined to the other portions of the belt body using overlapping seams 1204 and stitching 1206. In other embodiments, other joining methods can be used to connect the respiratory expansion panel 1202 to the belt body 102 including, but not limited to, known fasteners, adhesives and thermal welding. In still other embodiments, the respiratory expansion panel 1202 can comprise metal springs, rubber bungees, rubber cords or other known mechanical elements that can stretch elastically under tension.

The maximum amount of elongation $L_{ENG}$ that the respiratory expansion panel 1202 can provide without permanent deformation is given by $L_{ENG}=(L_{Max}-L_O)$. The stretch rate SR describes $L_{ENG}$ relative to the original length $L_O$ with the following relations: $SR=(L_{Eng}/L_O)=(L_{Max}-L_O)/L_O$. For example, a respiratory expansion panel 1202 having an original length $L_O=10$ inches and a maximum stretched length $L_{Max}=18.5$ inches will have an elongation $L_{ENG}=8.5$ inches and a stretch rate SR=0.85 or 85%.

The respiratory expansion panel 1202 in FIG. 12 is disposed in the belt body 102 adjacent to the second end portion 106. In other embodiments, the respiratory expansion panel 1202 can be disposed in the belt body adjacent to the first end portion 104, or multiple respiratory expansion panels can be spaced apart along the length of the belt body. For a desired total amount of belt elongation $L_{Tot}$, the belt body 102 can include a single respiration expansion panel 1202 with $L_{Eng}=L_{Tot}$, or alternatively, it can include N separate respiratory expansion panels wherein the sum of $L_{Eng}(n)$ for panels n=(1 . . . N)=$L_{Tot}$. For example, in one embodiment, the belt body 102 includes a single respiratory expansion panel 1202 made of elastic fabric having an original length $L_O>2$ inches. In another embodiment, the belt body 102 includes a single respiratory expansion panel 1202 made of elastic fabric having an original length $L_O$ within the range from 3.5 inches to 4.5 inches. In some embodiment, the respiratory expansion panel or panels 1202 can provide a total centerline elongation $L_{Tot}$ for all panels within the range from 1.7 inches to 4.5 inches. In other embodiments, the respiratory expansion panel or panels 1202 can provide a total centerline elongation $L_{Tot}$ within the range from 2.8 inches to 4.1 inches. In another embodiment, the belt body 102 includes a single respiratory expansion panel 1202 made of elastic fabric providing total elongation $L_{Tot}>=3.4$ inches. In still another embodiment, the respiratory expansion panel 1202 is made of elastic fabric having a stretch rate SR within the range from 80% to 90% and an original length $L_O>=4$ inches.

Figure 13A:
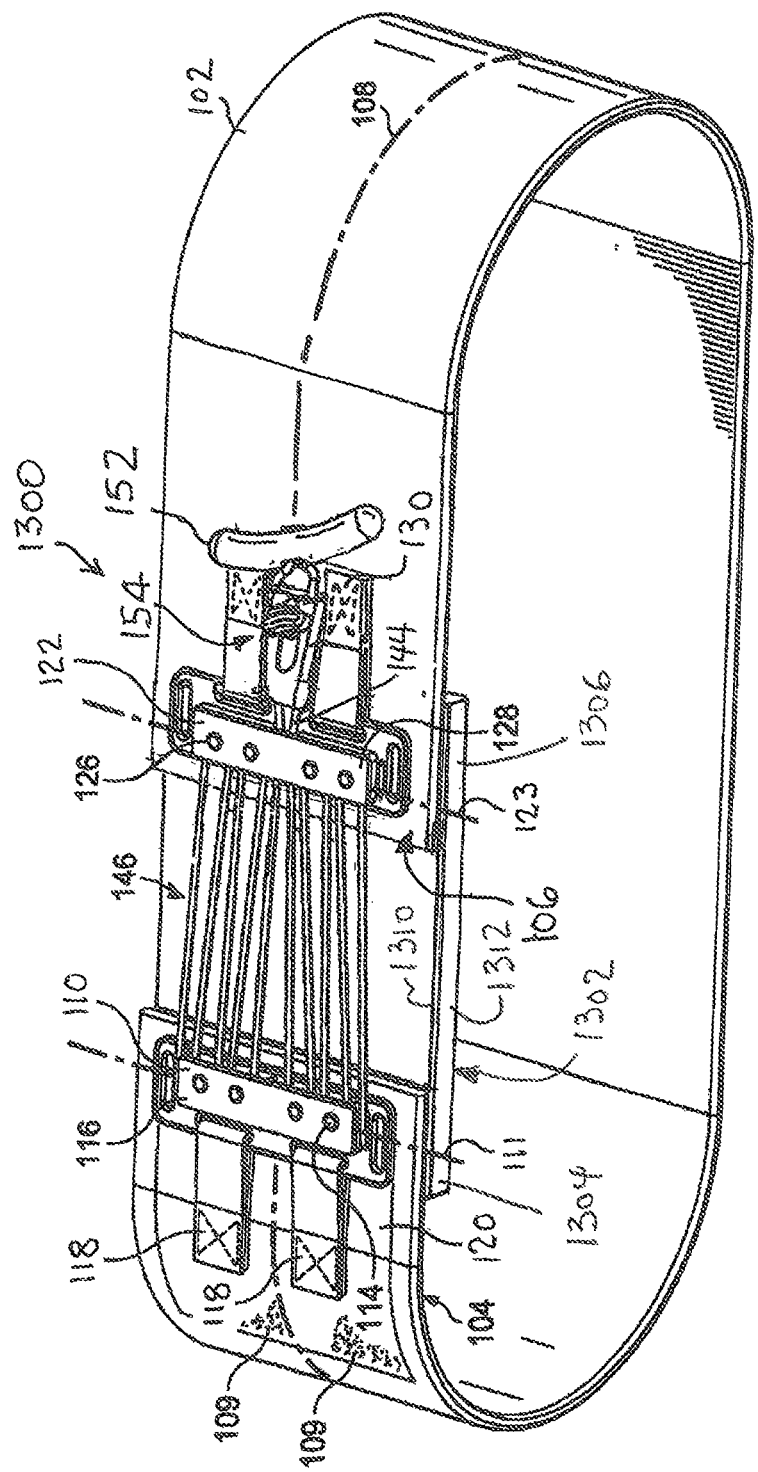
Figure 13B:
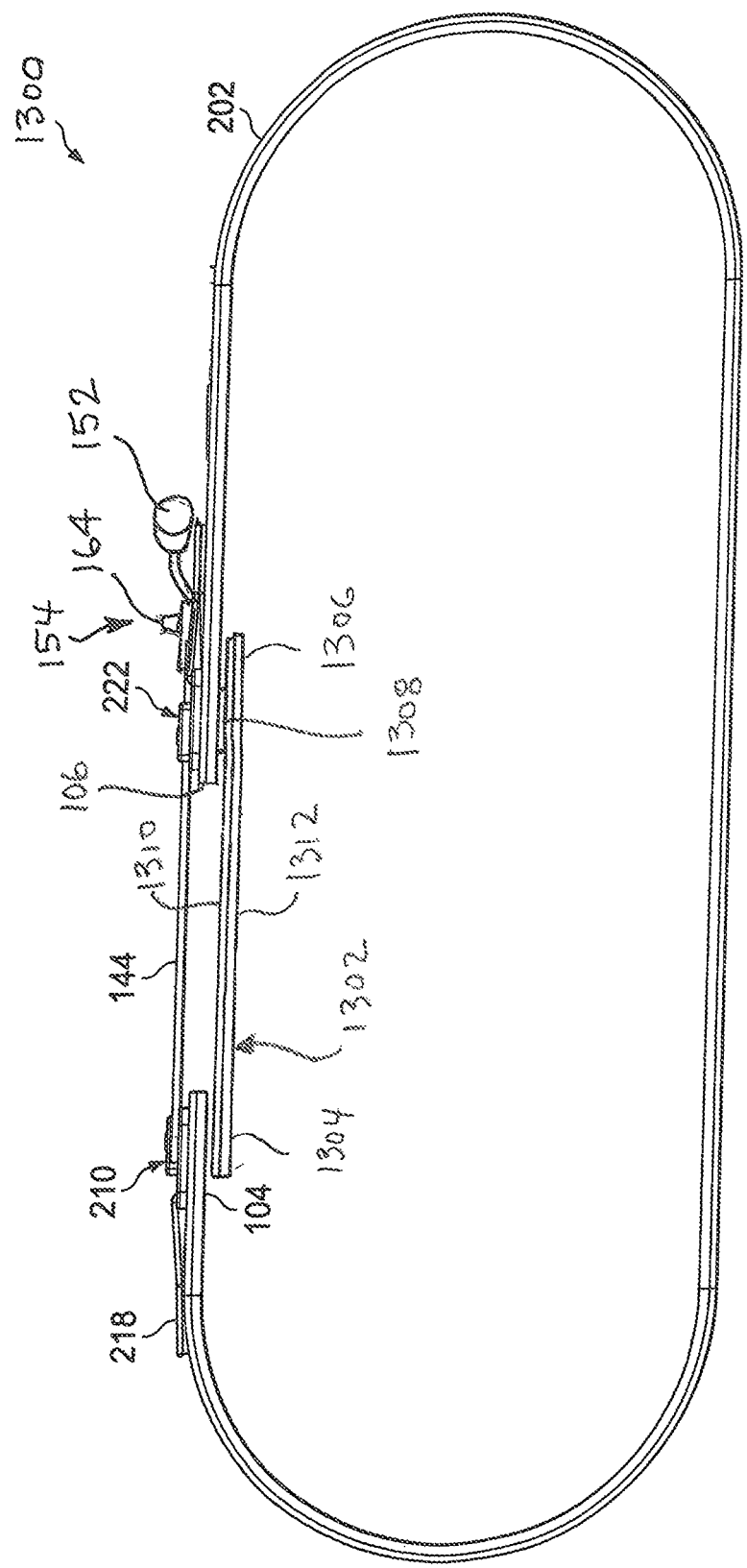

Referring now to FIGS. 13A and 13B, there is illustrated a compression belt 1300 in accordance with a still further aspect. Except as otherwise described, the compression belt 1300 is substantially similar in many respects to the belt 100 previously described, therefore common reference numbers are used for similar elements. Suspenders 701 can be included in some embodiments, but are not shown in the illustrated embodiment. The compression belt 1300 has at least two pulley banks 110 and 122 disposed, respectively, on end portions 104 and 106 as illustrated in FIGS. 13A and 13B. In some embodiments, the compression belt 1300 can have three pulley banks 110, 122 and 134 as previously disclosed. The compression belt 1300 can include a selectively releasable one-way cord lock mechanism 154 as previously disclosed; however, in embodiments having only two pulley banks, the one-way cord lock mechanism can be disposed adjacent to the second pulley bank 122 (as shown in FIG. 13A) rather than adjacent the third pulley bank (as shown, e.g., in FIG. 1). In embodiments having only two pulley banks, the flexible cord 144 can exit the second pulley bank 122 and go directly into the selectively releasable one-way cord-lock mechanism 154 and then to the pull handle 152.

The compression belt 1300 includes a friction-reducing protective pad 1302 disposed adjacent to the belt end portions 104 and 106 and spanning the gap between the end portions. The friction-reducing pad 1302 includes end portions 1304 and 1306 disposed adjacent to the corresponding belt end portions 104 and 106. A first one of the pad end portions 1304 or 1306 can be affixed to the corresponding one of the belt end portions 104 or 106 to prevent relative sliding movement therebetween, whereas the other (i.e., second) pad end portion is not affixed (i.e., non-affixed) to the corresponding second belt end portion, thereby allowing the second belt end portion to slide over the upper side of the second pad end portion when the pulley mechanism is activated to narrow the gap between the belt ends. In some embodiments, the affixing of one pad end portion 1304 or 1306 to the corresponding belt end portion 104 or 106 can be permanent, e.g., using known permanent attachment structures including, but not limited to, stitching, adhesives, fasteners, etc. In some such embodiments, the low-friction protective pad 1302 can comprise an extension of the belt body 102 (e.g., portion 132 in FIG. 1) having added features as later disclosed, such that the affixed end of the pad 1302 abuts the corresponding belt end portion. In other embodiments, the affixing of one pad end portion 1304 or 1306 to the corresponding belt end portion 104 or 106 can be selectively releasable, e.g., using known releasable attachment structures including, but not limited to, hook and loop material 1308 (e.g., VELCRO®), zippers, buttons, snap connectors, etc. When the friction-reducing protective pad 1302 is releasably affixed to the belt body 102, the pad can be removed for cleaning and/or replacement in case it becomes soiled, worn or damaged during use. For example, in the illustrated embodiment of FIGS. 13A and 13B, the first pad end 1306 is releasably affixed to the first belt end 106 using hook and loop material 1308 attached to the underside of the first belt end and the upper side of the first pad end 1306, whereas the second pad end 1304 is not affixed to the second belt end 104. Thus, when the pulley mechanism of the illustrated belt 1300 is activated, the first pad end portion 1306 and first belt end portion 106 cannot slide relative to one another, whereas the second belt end portion 104 can slide across the upper side of the protective pad 1302 (i.e., relative to the second pad end portion 1304), thus moving toward the first end portion as the belt tightens around the patient.

The friction-reducing protective pad 1302 includes two layers of material joined to one another, namely, an upper layer 1310 and a lower layer 1312. The material of the upper layer 1310 can be relatively harder and relatively stiffer (i.e., less flexible) compared to the material of the lower layer 1312. The material of the upper layer 1310 can have relatively lower coefficient of friction than the material of the lower layer 1312. In some embodiments, the material of the upper layer 1310 can be a high density polymer sheet and the material of the lower layer 1312 can be a low density plastic foam. In some other embodiments, the material of the upper layer 1310 can be a high density polymer sheet and the material of the lower layer 1312 can be the material of the belt body 102. In some further embodiments, the high density polymer sheet of upper layer 1310 can be a high density polyethylene (HDPE). In some further embodiments, the high density polymer sheet of upper layer 1310 can be a sheet of HDPE having a thickness of 0.040 inches. In other further embodiments, low density plastic foam of the lower layer 1312 can be a closed cell foam LD20™ manufactured by Zotefoams. In another embodiment, the material of the upper layer 1310 can have a thickness of 0.040 inches and the material of the lower layer 1312 can have a thickness of 0.250 inches. The material of the upper layer 1310 can provide a low-friction surface for sliding contact between the pad 1302 and the underside of the non-affixed end portion of the belt body. The material of the upper layer 1310 can be flexible enough to allow the protective pad 1302 to curve slightly to match the overall curve of the patient's body beneath the belt, but stiff enough to prevent localized bunching or "accordioning" of the protective pad during drawing together of the end portions 104, 106. The material of the upper layer 1312 is also hard enough to protect the underlying portions of the patient's anatomy from direct contact with the cords 144, 146 of the pulley mechanism. The material of the lower layer 1312 can be softer and more flexible than the material of the upper layer 1310 so the lower layer can better conform to the local contours of the patient's anatomy body and provide a softer feel compared to the relatively hard upper layer.

When the pulley mechanism of the compression belt 1300 is activated by pulling the handle 152, the belt end portions 104, 106 are drawn towards one another by the action of the cords 144, 146 and pulley banks 110, 122. In the absence of the friction-reducing protective pad 1302, under some circumstances the patient's anatomy disposed directly below the cords 146 can be pinched or squeezed by cords 146 and/or moving belt end portions 104, 106, thereby causing discomfort. In addition, due to friction with the patient's anatomy, the pulling effort on the activation handle 152 can be relatively high. When the friction-reducing protective pad 1302 is provided, the protective pad can remain stationary against the patient's anatomy (i.e., with the relatively soft lower layer 1312 in direct contact with the patient), thereby anchoring the affixed end portion of the belt body to also remain stationary relative to the patient, while the opposite, non-affixed end portion of the belt body can slide relative to the pad 1302 across the relatively stiff and relatively lower-friction upper layer 1310 across the gap toward the affixed end portion. Thus, the patient's anatomy is better protected by the friction-reducing protective pad 1302 and the pulling force required to activate the compression belt 1300 is reduced due to the relatively lower friction of the belt body 102 sliding over the low-friction upper layer 1310.

Although the preferred embodiment has been described in detail, it should be understood that various changes, substitutions and alterations can be made therein without departing from the spirit and scope of the invention as defined by the appended claims.

It will be appreciated by those skilled in the art having the benefit of this disclosure that new and improved compression belts for selective chest compression following thoracic and cardiothoracic surgery, for selective abdominal compression following abdominal surgery, for stabilization of rib fractures and for emergency stabilization of pelvic fractures are described. It should be understood that the drawings and detailed description herein are to be regarded in an illustrative rather than a restrictive manner, and are not intended to be limiting to the particular forms and examples disclosed. On the contrary, included are any further modifications, changes, rearrangements, substitutions, alternatives, design choices, and embodiments apparent to those of ordinary skill in the art, without departing from the spirit and scope hereof, as defined by the following claims. Thus, it is intended that the following claims be interpreted to embrace all such further modifications, changes, rearrangements, substitutions, alternatives, design choices, and embodiments.

What is claimed is:

1. A compression belt for encircling a selected portion of a patient's body and providing temporary circumferential compression of the selected portion of the patient's body, the compression belt comprising:
    an elongated belt body having a continuous length with opposing first and second free end portions and defining a centerline extending therebetween, the belt body adapted to be wrapped circumferentially around the selected portion of the patient's body;
    a first pulley bank affixed to the first end portion, the first pulley bank including at least two pulleys arranged perpendicular to the centerline of the belt body;
    a second pulley bank affixed to the second end portion, the second pulley bank including at least two pulleys arranged perpendicular to the centerline of the belt body;
    a third pulley bank affixed to the belt body at a fixed distance from the second pulley bank, the third pulley bank including at least two pulleys arranged perpendicular to the centerline of the belt body;
    a flexible cord interconnecting the first, second and third pulley banks, the cord having
        a first cord portion extending between the pulleys of the first and second pulley banks in alternation,
        a second cord portion connected to the first cord portion and extending between the pulleys of the first and third pulley banks, and
        a third cord portion connected to the second cord portion and extending away from the third pulley bank;
    a handle connected to the third cord portion, whereby withdrawing the third cord portion from the third pulley bank by pulling the handle away from the third pulley bank causes a shortening of the first cord portion such that the first and second pulley banks move closer together along with the first and second free end portions to which the respective pulley banks are affixed, thereby circumferentially tightening the belt body around the selected portion of the patient's body and circumferentially compressing the selected portion of the patient's body; and
    a buffer attached to an inner surface of the body belt, the buffer being formed of a flexible and compressible material having a width $W_B$ measured in a direction parallel to the lateral width $W_L$ of the belt body, a length $L_B$ measured in a direction parallel to the centerline of the belt body, and a thickness $T_B$ measured perpendicular to $W_B$ and $T_B$; and wherein circumferential tightening of the belt body causes compression of the compressible material of the buffer in the thickness direction against an adjacent portion of the patient's body, wherein an inward pressure is exerted on the adjacent portion of the patient's body by the buffer.

2. A compression belt according to claim 1, wherein the buffer is formed of a plastic foam material having a density in the range from 1.1 pounds per cubic foot to 1.5 pounds per cubic foot and an indentation load deflection (ILD) in the range from 50 pounds to 80 pounds.

3. A compression belt according to claim 1, wherein the buffer has a width $W_B$ less than or equal to the lateral width $W_L$ of the belt body.

4. A compression belt according to claim 1, wherein the buffer has a width $W_B$ greater than 1.25 times the lateral width $W_L$ of the belt body.

5. A compression belt according to claim 4, wherein the buffer has a rectangular configuration with a uniform width $W_B$ and a uniform length $L_B$.

6. A compression belt according to claim 4, wherein the buffer has a heart-shaped configuration that is at least partially visible from the front side of the belt body.

7. A compression belt according to claim 6, wherein the heart-shaped buffer has a width $W_B$ at least 1.4 times the lateral width $W_L$ of the belt body.

8. A compression belt according to claim 6, wherein the heart shaped buffer has a visible red color.

9. A compression belt according to claim 6, wherein the heart shaped buffer is formed of an unjacketed plastic foam material having a density of at least 1.3 pounds per cubic foot and an indentation load deflection (ILD) of at least 70 pounds.

10. A compression belt according to claim 6, wherein the heart shaped buffer includes a fabric or plastic jacket over the flexible material.

11. A compression belt according to claim 4, wherein the buffer is formed of an unjacketed plastic foam material having a density of at least 1.3 pounds per cubic foot and an indentation load deflection (ILD) of at least 70 pounds.

12. A compression belt according to claim 1, further comprising:
a selectively releasable one-way cord lock mechanism connected to the belt body, the cord lock mechanism including
a frame defining a cord passage through which the third cord portion is routed after leaving the third pulley bank,
a locking member mounted in the frame and movable between a locked position and a released position, the third cord portion being routed against the locking member so as to bias the locking member toward the locked position, and
a release member connected to the locking member for moving the locking member between the locked position and the released position;
whereby the locking member,
when in either the locked position or the released position, allows withdrawal of the third cord portion from the third pulley bank to compress the selected portion of the patient's body,
when in the locked position, prevents the third cord portion from retracting into the third pulley bank to maintain compression of the selected portion of the patient's body, and
when in the released position, allows the third cord portion to retract into the third pulley bank to discontinue compression of the selected portion of the patient's body.

13. A compression belt for encircling a selected portion of a patient's body and providing temporary circumferential compression of the selected portion of the patient's body, the compression belt comprising:
an elongated belt body having a continuous length with opposing first and second free end portions and defining a centerline extending therebetween, the belt body adapted to be wrapped circumferentially around the selected portion of the patient's body;
a first pulley bank affixed to the first end portion, the first pulley bank including at least two pulleys arranged perpendicular to the centerline of the belt body;
a second pulley bank affixed to the second end portion, the second pulley bank including at least two pulleys arranged perpendicular to the centerline of the belt body;
a flexible cord interconnecting the first and second pulley banks, the cord having
a first cord portion extending between the pulleys of the first and second pulley banks in alternation, and
a second cord portion connected to the first cord portion and extending away from the second pulley bank;
a handle connected to the second cord portion, whereby withdrawing the second cord portion from the second pulley bank by pulling the handle causes a shortening of the first cord portion such that the first and second pulley banks move closer together along with the first and second free end portions to which the respective pulley banks are affixed, thereby circumferentially tightening the belt body around the selected portion of the patient's body and circumferentially compressing the selected portion of the patient's body; and
a buffer attached to an inner surface of the body belt, the buffer being formed of a flexible and compressible material having a width $W_B$ measured in a direction parallel to the lateral width $W_L$ of the belt body, a length $L_B$ measured in a direction parallel to the centerline of the belt body, and a thickness $T_B$ measured perpendicular to $W_B$ and $T_B$; and
wherein circumferential tightening of the belt body causes compression of the compressible material of the buffer in the thickness direction against an adjacent portion of the patient's body, wherein an inward pressure is exerted on the adjacent portion of the patient's body by the buffer.

14. A compression belt according to claim 13 wherein the buffer has a width $W_B$ less than or equal to the lateral width $W_L$ of the belt body.

15. A compression belt according to claim 13 wherein the buffer has a width $W_B$ greater than 1.25 times the lateral width $W_L$ of the belt body.

16. A compression belt according to claim 15, wherein the buffer has a heart-shaped configuration that is at least partially visible from the front side of the belt body.

17. A compression belt for encircling a selected portion of a patient's body and providing temporary circumferential compression of the selected portion of the patient's body, the compression belt comprising:

an elongated belt body having a continuous length with opposing first and second free end portions and defining a centerline extending therebetween, the belt body adapted to be wrapped circumferentially around the selected portion of the patient's body;

a first pulley bank affixed to the first end portion, the first pulley bank including at least two pulleys arranged perpendicular to the centerline of the belt body;

a second pulley bank affixed to the second end portion, the second pulley bank including at least two pulleys arranged perpendicular to the centerline of the belt body;

a third pulley bank affixed to the belt body at a fixed distance from the second pulley bank, the third pulley bank including at least two pulleys arranged perpendicular to the centerline of the belt body;

a flexible cord interconnecting the first, second and third pulley banks, the cord having
- a first cord portion extending between the pulleys of the first and second pulley banks in alternation,
- a second cord portion connected to the first cord portion and extending between the pulleys of the first and third pulley banks, and
- a third cord portion connected to the second cord portion and extending away from the third pulley bank;

a handle connected to the third cord portion, whereby withdrawing the third cord portion from the third pulley bank by pulling the handle away from the third pulley bank causes a shortening of the first cord portion such that the first and second pulley banks move closer together along with the first and second free end portions to which the respective pulley banks are affixed, thereby tightening the belt body around the selected portion of the patient's body and circumferentially compressing the selected portion of the patient's body; and wherein the belt body further includes at least one respiratory expansion panel having an original length $L_O$ that can stretch elastically in the centerline direction to a maximum length $L_{Max}$ when circumferential tension is applied to the belt body and can return to the original length $L_O$ when the circumferential tension is released.

18. A compression belt according to claim 17, wherein the respiratory expansion panel is a section of elastic fabric that spans the full width of the belt body and is joined to the other portions of the belt body using overlapping seams and stitching.

19. A compression belt according to claim 17, wherein the respiratory expansion panel has an original length $L_O$ greater than 2 inches and a stretch rate SR of at least 80%.

20. A compression belt according to claim 17, wherein the at least one respiratory expansion panel has a total elongation $L_{Tot}$ greater than or equal to 3.4 inches.

* * * * *